United States Patent
Yasuoka et al.

(10) Patent No.: US 10,723,769 B2
(45) Date of Patent: Jul. 28, 2020

(54) IMMUNOGLOBULIN-BINDING PROTEIN AND AFFINITY CARRIER USING SAME

(71) Applicants: JSR CORPORATION, Minato-ku (JP); JSR LIFE SCIENCES CORPORATION, Minato-ku (JP)

(72) Inventors: Jun-ichi Yasuoka, Minato-ku (JP); Takashi Ichii, Minato-ku (JP); Satoshi Nakamura, Minato-ku (JP); Tomonori Shiotani, Minato-ku (JP); Kaori Itaya, Minato-ku (JP)

(73) Assignees: JSR CORPORATION, Minato-ku (JP); JSR LIFE SCIENCES CORPORATION, Minato-ku (JP)

( * ) Notice: Subject to any disclaimer, the term of this patent is extended or adjusted under 35 U.S.C. 154(b) by 222 days.

(21) Appl. No.: 15/561,332

(22) PCT Filed: Mar. 24, 2016

(86) PCT No.: PCT/JP2016/059282
§ 371 (c)(1),
(2) Date: Sep. 25, 2017

(87) PCT Pub. No.: WO2016/152946
PCT Pub. Date: Sep. 29, 2016

(65) Prior Publication Data
US 2018/0105560 A1    Apr. 19, 2018

(30) Foreign Application Priority Data
Mar. 26, 2015    (JP) .................................. 2015-063519

(51) Int. Cl.
| | | |
|---|---|---|
| *C07K 14/31* | (2006.01) | |
| *C07K 1/22* | (2006.01) | |
| *C07K 14/195* | (2006.01) | |
| *C07K 17/04* | (2006.01) | |
| *C12N 15/09* | (2006.01) | |
| *C12N 5/10* | (2006.01) | |
| *G01N 33/68* | (2006.01) | |
| *C07K 16/12* | (2006.01) | |
| *C07K 17/08* | (2006.01) | |

(52) U.S. Cl.
CPC ............. *C07K 14/195* (2013.01); *C07K 1/22* (2013.01); *C07K 14/31* (2013.01); *C07K 16/1203* (2013.01); *C07K 17/04* (2013.01); *C07K 17/08* (2013.01); *C12N 5/10* (2013.01); *C12N 15/09* (2013.01); *G01N 33/6854* (2013.01)

(58) Field of Classification Search
None
See application file for complete search history.

(56) References Cited

U.S. PATENT DOCUMENTS

| | | |
|---|---|---|
| 2010/0063256 A1 | 3/2010 | Spector |
| 2010/0168395 A1 | 7/2010 | Sato |
| 2010/0286373 A1 | 11/2010 | Majima et al. |
| 2012/0184711 A1 | 7/2012 | Sato |
| 2013/0046056 A1 | 2/2013 | Spector et al. |
| 2014/0046037 A1 | 2/2014 | Spector |
| 2014/0100356 A1 | 4/2014 | Yoshida et al. |
| 2014/0107315 A1 | 4/2014 | Yoshida et al. |
| 2014/0179898 A1 | 6/2014 | Honda et al. |
| 2014/0296434 A1 | 10/2014 | Spector et al. |
| 2015/0080558 A1 | 3/2015 | Spector et al. |
| 2015/0252085 A1 | 9/2015 | Spector et al. |
| 2016/0159855 A1 | 6/2016 | Rodrigo et al. |
| 2016/0159857 A1 | 6/2016 | Rodrigo et al. |
| 2016/0168194 A1 | 6/2016 | Spector et al. |
| 2016/0207966 A1 | 7/2016 | Ander et al. |
| 2017/0320922 A1 | 11/2017 | Ander et al. |
| 2017/0333811 A1* | 11/2017 | Yoda ..................... B01D 15/08 |
| 2018/0244729 A1 | 8/2018 | Rodrigo et al. |

FOREIGN PATENT DOCUMENTS

| | | |
|---|---|---|
| EP | 2 495 253 A1 | 9/2012 |
| EP | 2 532 672 A2 | 12/2012 |
| EP | 2 532 672 A3 | 12/2012 |
| EP | 2 690 173 A1 | 1/2014 |
| EP | 2 728 000 A1 | 5/2014 |
| JP | 6-281638 A | 10/1994 |

(Continued)

OTHER PUBLICATIONS

Baker et al. "Protein Structure Prediction and Structural Genomics" Science 294 (5540) pp. 93-96 (Year: 2001).*

(Continued)

*Primary Examiner* — Daniel E Kolker
*Assistant Examiner* — James L Rogers
(74) *Attorney, Agent, or Firm* — Oblon, McClelland, Maier & Neustadt, L.L.P.

(57) ABSTRACT

Provided is an affinity chromatography carrier that maintains high immunoglobulin-binding capacity and high alkali resistance. An immunoglobulin-binding protein including at least one modified immunoglobulin-binding domain, the modified immunoglobulin-binding domain being a polypeptide consisting of an amino acid sequence of an immunoglobulin-binding domain selected from the group consisting of the B domain, Z domain, C domain, and variants thereof of *Staphylococcus aureus* protein A, in which at least one amino acid residue is inserted between positions corresponding to the 3-position and position 4 of the amino acid sequence of the B domain, Z domain or C domain.

13 Claims, No Drawings

Specification includes a Sequence Listing.

(56) References Cited

FOREIGN PATENT DOCUMENTS

| | | | |
|---|---|---|---|
| JP | 2002-527107 A | 8/2002 | |
| JP | 2002-527107 A5 | 8/2002 | |
| JP | 2007-252368 A | 10/2007 | |
| JP | 2007-252368 A5 | 10/2007 | |
| JP | 2012-254981 A | 12/2012 | |
| JP | 2013-534532 A | 9/2013 | |
| JP | 5298242 B2 | 9/2013 | |
| JP | 5345539 B3 | 11/2013 | |
| WO | WO 00/23580 A1 | 4/2000 | |
| WO | WO-2007019376 A2 * | 2/2007 | ........... A61K 49/085 |
| WO | WO 2008/039141 A1 | 4/2008 | |
| WO | WO 2008/143199 A1 | 11/2008 | |
| WO | WO 2012/003474 A2 | 1/2012 | |
| WO | WO 2012/133342 A1 | 10/2012 | |
| WO | WO 2015/005859 A1 | 1/2015 | |
| WO | WO 2015/034000 A1 | 3/2015 | |

OTHER PUBLICATIONS

Atwood "The babel of Bioinformatics" Science 290(5491) pp. 471-473 (Year: 2000).*

International Search Report dated Jun. 21, 2016, in PCT/JP2016/059282 filed Mar. 23, 2016.

Deis et al., "Multiscale conformational heterogeneity in the protein-binding domains of staphylococcal protein A: Possible determinant of functional plasticity[§]", NIH Public Access Author Manuscript, (2014), 25 pages.

Guelich et al., "Stability towards alkaline conditions can be engineered into a protein ligand", Journal of Biotechnology, vol. 80, (2000), pp. 169-178.

Extended European Search Report dated Oct. 16, 2018 in corresponding European Patent Application No. 16768849.8, 10 pages.

* cited by examiner

IMMUNOGLOBULIN-BINDING PROTEIN AND AFFINITY CARRIER USING SAME

TECHNICAL FIELD

The present invention relates to an immunoglobulin-binding protein, an affinity carrier using the same, and a method for isolating an immunoglobulin and a method for producing an antibody medicine, both of which methods use the affinity carrier.

BACKGROUND ART

Affinity chromatography is chromatography that uses a column packed with a ligand-immobilized carrier, in which a substance (ligand) that specifically binds to a substance intended to be separated or purified is immobilized on an insoluble carrier. Affinity chromatography is used for, for example, separation and purification of bio-related substances such as proteins and nucleic acids (Patent Literature 1). As the carrier for affinity chromatography, for example, crosslinked particles of sugar chains represented by agarose gel, or particles containing a synthetic polymer as a main component are used.

In the production of an affinity chromatography carrier, it is necessary to immobilize a ligand, which is a substance capable of binding specifically to an intended substance, to the carrier. Staphylococcus aureus protein A (SpA) and variants thereof are known as representative affinity chromatography ligands having a binding capacity specific to immunoglobulins. Since SpA has an ability to bind to the Fc region of an immunoglobulin without noticeably affecting the high selectivity of the immunoglobulin for antigens, immunoglobulins and Fc region-containing proteins can be efficiently captured and purified thereby.

Natural-type SpA contains five domains, namely, E, D, A, B and C, in sequence from the N-terminal, as domains having a binding capacity for immunoglobulins. These domains and the Z domain, which is a modified domain of the B domain, are used as the affinity chromatography ligands. Furthermore, for the purpose of increasing the immunoglobulin-binding capacity, it is also common to use a product obtained by linking two or more of the above-mentioned domains together, as a ligand.

It is known that the above-mentioned immunoglobulin-binding domains of SpA respectively contain three α-helix structures, and among these, two α-helix portions on the N-terminal side contribute to the binding to immunoglobulins. Furthermore, in regard to the B and C domains among the above-mentioned domains, it has been reported that a turn structure is formed by Asn at the position 3 and Lys at the position 4 of the N-terminal (Non-Patent Literature 1). Therefore, in regard to a ligand obtained by linking multiple units of the B domain, the C domain, or the Z domain, which is a modified domain of the B domain, it is speculated that the various domains are linked in an arrangement of being crooked from each other due to the turn structures, and the ligand causes steric hindrance attributed to this crooked arrangement. This steric hindrance causes a serious problem in producing an affinity chromatography carrier that employs a repeated structure of the B domain, the C domain or the Z domain as a ligand. That is, the immunoglobulin-binding capacity of the ligand remains low because of the steric hindrance mentioned above, and consequently, a large amount of carrier is required in order to purify a certain amount of immunoglobulins. Affinity chromatography carriers that employ SpA as a ligand are very expensive in many cases, and requiring a large amount of carrier is not desirable from the viewpoint of production cost.

Affinity chromatography carriers are usually used repeatedly in the applications related to bioseparation. Therefore, usually, a cleaning process known as cleaning-in-place (CIP), which is intended for returning a carrier to the original state by eliminating contaminants, is repeatedly carried out during use. Regarding the reagent for the CIP, for example, an alkaline liquid of, e.g., sodium hydroxide is used. However, for those affinity chromatography carriers that use a protein as a ligand, such alkaline conditions are harsh, and the ligands may lose the binding capacity for target molecules as a result of deactivation or cleavage of the ligands. In regard to the deactivation of ligands under such alkaline conditions, deamidation of Asn and Gln residues is widely known as a main cause of the deactivation. Particularly, it has been reported that Asn is highly sensitive to alkaline conditions, and deamidation thereof is structure-dependent and it frequently occurs at an amino acid sequence site represented by Asn-Gly or Asn-Ser (Non-Patent Literature 2).

An example of the prior art technologies for avoiding the deactivation of ligands under alkaline conditions as described above may include obtaining a ligand having decreased sensitivity to alkali as a result of deletion or modification of Asn residues. By using such a ligand, an affinity chromatography carrier that can maintain the immunoglobulin-binding capacity even after a CIP using an alkaline solution has been carried out several times, is provided. For example, in Patent Literature 2, there is provided a ligand for an affinity chromatography carrier, the ligand including the B domain, the C domain or the Z domain of SpA, and the ligand including deletion of at least three consecutive amino acids on the N-terminal side starting from the position 1 or the position 2 of at least one domain. Furthermore, in Patent Literature 3, there is provided a ligand for an affinity chromatography carrier, the ligand including the C domain of SpA in which consecutive amino acids from the position 3 to the position 6 on the N-terminal side have been deleted. In Patent Literature 4, there is provided a ligand for affinity chromatography carrier, the ligand having a modified Asn residue in the Z domain or the B domain of SpA. However, the prior art technologies described above are primarily purported to increase the alkali resistance of carriers, and there is no mention about increasing the immunoglobulin-binding capacity of carriers.

CITATION LIST

Patent Literature

Patent Literature 1: JP H6-281638 A
Patent Literature 2: JP 2012-254981 A
Patent Literature 3: JP 5345539 B
Patent Literature 4: JP 2002-527107 A

Non Patent Literature

Non-Patent Literature 1: Structure, 2014, 22:1467-1477.
Non-Patent Literature 2: Journal of Biotechnology, 2000, 80:169-178

SUMMARY OF INVENTION

Technical Problem

There is a demand for an affinity carrier that retains high immunoglobulin-binding capacity and high alkali resistance and is efficient and highly economically valuable. An aspect of the present invention relates to providing a novel ligand for an affinity carrier, the ligand having an increased binding capacity for immunoglobulins. Another aspect of the present invention relates to providing an affinity carrier that can maintain the high immunoglobulin-binding capacity mentioned above, even when a CIP using an alkaline solution is repeatedly carried out.

Solution to Problem

Therefore, according to an aspect of the present invention, there is provided an immunoglobulin-binding protein. This immunoglobulin-binding protein includes at least one modified immunoglobulin-binding domain, and the modified immunoglobulin-binding domain is a polypeptide consisting of an amino acid sequence in which at least one amino acid residue is inserted between the positions corresponding to the position 3 and position 4 of the amino acid sequence of the B domain, the Z domain or the C domain, in the amino acid sequence of an immunoglobulin-binding domain selected from the group consisting of the B domain, Z domain, C domain, and variants thereof of *Staphylococcus aureus* protein A (SpA).

According to an embodiment of the immunoglobulin-binding protein of the present invention, the immunoglobulin-binding domain selected from the group consisting of B domain, Z domain, C domain, and variants thereof is an immunoglobulin-binding domain consisting of an amino acid sequence set forth in any one of SEQ ID NO: 1 to SEQ ID NO: 3, or an amino acid sequence having at least 70% identity with the aforementioned amino acid sequences.

According to an embodiment of the immunoglobulin-binding protein of the present invention, the at least one modified immunoglobulin-binding domain is selected from the group consisting of the following:

a polypeptide being an immunoglobulin-binding domain consisting of an amino acid sequence set forth in SEQ ID NO: 1 or an amino acid sequence having at least 70% identity with the aforementioned amino acid sequence, in which at least one amino acid residue is inserted between positions corresponding to the position 3 and position 4 of the amino acid sequence set forth in SEQ ID NO: 1;

a polypeptide being an immunoglobulin-binding domain consisting of an amino acid sequence set forth in SEQ ID NO: 2 or an amino acid sequence having at least 70% identity with the aforementioned amino acid sequence, in which at least one amino acid residue is inserted between positions corresponding to the position 3 and position 4 of the amino acid sequence set forth in SEQ ID NO: 2; and a polypeptide being an immunoglobulin-binding domain consisting of an amino acid sequence set forth in SEQ ID NO: 3 or an amino acid sequence having at least 70% identity with the aforementioned amino acid sequence, in which at least one amino acid residue is inserted between positions corresponding to the position 3 and position 4 of the amino acid sequence set forth in SEQ ID NO: 3.

According to an embodiment of the immunoglobulin-binding protein of the present invention, the at least one amino acid residue is at least one selected from the group consisting of Ala, Arg, Asp, Gln, Glu, His, Met, Thr, Val, Phe, Leu, Ile, Pro, Trp, and Tyr.

According to an embodiment of the immunoglobulin-binding protein of the present invention, the immunoglobulin-binding domain consisting of an amino acid sequence having at least 70% identity with the amino acid sequence set forth in any one of SEQ ID NO: 1 to SEQ ID NO: 3 is a Val1/Ala29 variant.

According to an embodiment, the immunoglobulin-binding protein of the present invention includes 2 to 12 units of the modified immunoglobulin-binding domain.

According to another aspect of the present invention, there is provided a polynucleotide encoding the mutated immunoglobulin-binding protein.

According to another aspect of the present invention, there is provided a vector including the polynucleotide.

According to another aspect of the present invention, there is provided a recombinant including the vector.

According to still another aspect of the present invention, there is provided a method for producing an immunoglobulin-binding protein, the method including expressing the polynucleotide by means of a cell-free protein synthesis system, or expressing the polynucleotide in the recombinant described above.

According to still another aspect of the present invention, there is provided a method for producing an immunoglobulin-binding protein. This method is a method including inserting, with regard to an amino acid sequence of an immunoglobulin-binding domain selected from the group consisting of the B domain, Z domain, C domain, and variants thereof of *Staphylococcus aureus* Protein A, at least one amino acid residue between positions corresponding to the position 3 and position 4 of the amino acid sequence of the B domain, Z domain or C domain.

According to another aspect of the present invention, there is provided a method for increasing the immunoglobulin-binding capacity of an immunoglobulin-binding protein. This method is a method including inserting, with regard to an amino acid sequence of an immunoglobulin-binding domain selected from the group consisting of the B domain, Z domain, C domain, and variants thereof of *Staphylococcus aureus* Protein A, at least one amino acid residue between positions corresponding to the position 3 and position 4 of the amino acid sequence of the B domain, Z domain or C domain.

According to an embodiment of the method for producing an immunoglobulin-binding protein and the method for increasing the immunoglobulin-binding capacity of the present invention, the immunoglobulin-binding domain selected from the group consisting of the B domain, Z domain, C domain, and variants thereof is an immunoglobulin-binding domain consisting of an amino acid sequence set forth in any one of SEQ ID NO: 1 to SEQ ID NO: 3, or an amino acid sequence having at least 70% identity with the aforementioned amino acid sequences.

According to an embodiment, the method for producing an immunoglobulin-binding protein and the method for increasing the immunoglobulin-binding capacity of the present invention includes:

inserting, with regard to an immunoglobulin-binding domain consisting of an amino acid sequence set forth in SEQ ID NO: 1 or an amino acid sequence having at least 70% identity with the amino acid sequence set forth in SEQ ID NO: 1, at least one amino acid residue between positions corresponding to the position 3 and position 4 of the amino acid sequence set forth in SEQ ID NO: 1;

inserting, with regard to an immunoglobulin-binding domain consisting of an amino acid sequence set forth in SEQ ID NO: 2 or an amino acid sequence having at least 70% identity with the amino acid sequence set forth in SEQ ID NO: 2, at least one amino acid residue between positions corresponding to the position 3 and position 4 of the amino acid sequence set forth in SEQ ID NO: 2; or inserting, with regard to an immunoglobulin-binding domain consisting of an amino acid sequence set forth in SEQ ID NO: 3 or an amino acid sequence having at least 70% identity with the amino acid sequence set forth in SEQ ID NO: 3, at least one amino acid residue between positions corresponding to the position 3 and position 4 of the amino acid sequence set forth in SEQ ID NO: 3.

According to an embodiment of the method for producing an immunoglobulin-binding protein and the method for increasing the immunoglobulin-binding capacity of the present invention, the at least one amino acid residue is at least one selected from the group consisting of Ala, Arg, Asp, Gln, Glu, His, Met, Thr, Val, Phe, Leu, Ile, Pro, Trp, and Tyr.

According to an embodiment of the method for producing an immunoglobulin-binding protein and the method for increasing the immunoglobulin-binding capacity of the present invention, the immunoglobulin-binding domain consisting of an amino acid sequence having at least 70% identity with the amino acid sequence set forth in any one of SEQ ID NO: 1 to SEQ ID NO: 3, is a Val1/Ala29 variant.

According to an embodiment, the method for producing an immunoglobulin-binding protein and the method for increasing the immunoglobulin-binding capacity of the present invention further includes linking 2 to 12 units of the immunoglobulin-binding domain having at least one amino acid residue inserted therein.

According to another aspect of the present invention, there is provided an affinity carrier including the immunoglobulin-binding protein immobilized on a base material insoluble in water.

According to another aspect of the present invention, there is provided a method for isolating an immunoglobulin, the method including using the affinity carrier.

According to another aspect of the present invention, there is provided a method for producing an antibody medicine, the method including using the affinity carrier.

Advantageous Effects of Invention

The mutated immunoglobulin-binding protein of the present invention is useful as a ligand for an affinity chromatography carrier. This mutated immunoglobulin-binding protein can be immobilized on an insoluble carrier when a reactive side chain such as an amino group, a thiol group or a carboxyl group included in the protein is chemically bonded to a functional group existing on the surface of the carrier. This mutated immunoglobulin-binding protein has high immunoglobulin-binding capacity, and can maintain high immunoglobulin-binding capacity even after a CIP using an alkaline solution is repeatedly carried out. Therefore, an affinity chromatography carrier that uses this mutated immunoglobulin-binding protein as a ligand is such that, for example, when the carrier is used for the purification of an immunoglobulin, a larger amount of the immunoglobulin can be purified using a certain amount of the carrier, and also, since the dynamic binding capacity of the immunoglobulin does not easily decrease even if the carrier is repeatedly used, the carrier consequently allows implementation of an immunoglobulin purification process at low cost.

DESCRIPTION OF EMBODIMENTS

All the patent documents, non-patent documents, and other publications cited in the present specification are entirely incorporated herein by reference.

According to the present specification, the sequence identity of amino acid sequences and nucleotide sequences is calculated by the Lipman-Pearson method (Science, 227, 1435-41, 1985). Specifically, the sequence identity is computed by performing an analysis using a homology analysis (Search Homology) program of a genetic information processing software, GENETYX-WIN (Ver. 5.1.1; software development), by setting the unit size to compare (ktup) as 2.

According to the present specification, the phrase "at least 70% identity" in connection with amino acid sequences and nucleotide sequences means identity of 70% or higher, preferably identity of 80% or higher, more preferably identity of 85% or higher, even more preferably identity of 90% or higher, still more preferably identity of 95% or higher, even more preferably identity of 98% or higher, and still more preferably identity of 99% or higher.

According to the present specification, the term "corresponding positions" on amino acid sequences and nucleotide sequences can be determined by aligning a target sequence and a reference sequence (for example, an amino acid sequence set forth in SEQ ID NO 3) so as to impart maximum homology to conserved amino acid residues or nucleotides present in various amino acid sequences or nucleotide sequences. Alignment can be carried out using a known algorithm, and the procedure is known to those skilled in the art. For example, the alignment can be carried out manually based on the Lipman-Pearson method described above; however, the alignment can be carried out using Clustal W Multiple Alignment program (Thompson, J. D, et al., 1994, Nucleic Acids Res., 22:4673-4680) under default settings. Alternatively, Clustal W2 or Clustal Omega, which are revised editions of Clustal W, can also be used. Clustal W, Clustal W2, and Clustal Omega can be utilized, for example, on the website of European Bioinformatics Institute (EBI [www.ebi.ac.uk/index.html]), or on the website of DNA Data Bank of Japan (DDBJ [www.ddbj.nig.ac.jp/Welcome-j.html]) operated by Japanese National Institute of Genetics.

The "immunoglobulin-binding protein" according to the present specification refers to a protein having a binding capacity for immunoglobulins. The "immunoglobulin-binding domain" according to the present specification refers to a domain involved in immunoglobulin binding, the domain being included in an immunoglobulin-binding protein, and examples thereof include the A domain, B domain, C domain, D domain, E domain, and Z domain, which is a modified domain of the B domain, of *Staphylococcus aureus* protein A (SpA).

1. Affinity Chromatography Carrier 1.1. Mutated Immunoglobulin-Binding Protein

The mutated immunoglobulin-binding protein of the present invention includes at least one modified immunoglobulin-binding domain derived from the B domain, C domain or Z domain of SpA. This modified immunoglobulin-binding domain is a polypeptide consisting of an amino acid sequence in which at least one amino acid residue is inserted between an Asn residue at a position corresponding to the position 3 and a Lys residue at a position corresponding to the position 4 of the amino acid sequence of the B domain, Z domain or C domain. The mutated immunoglobulin-binding protein of the present invention can be used as a ligand for an affinity carrier.

Examples of a parent domain of the modified immunoglobulin-binding domain included in the mutated immunoglobulin-binding protein of the present invention include the B domain, Z domain, C domain, and variants thereof, which are domains having an immunoglobulin-binding capacity for SpA. Among these, the B domain, Z domain, and C domain are preferred. The B domain, Z domain, and C domain of SpA are polypeptides consisting of amino acid sequences set forth in SEQ ID NO: 1, SEQ ID NO: 2, and SEQ ID NO: 3, respectively. These domains have an Asn residue at the position 3 and a Lys residue at the position 4 in the amino acid sequences, and have a turn structure composed of these amino acid residues.

Regarding a variant of the B domain, Z domain or C domain that can be used as the parent domain, a polypeptide that consists of an amino acid sequence having at least 70% identity with an amino acid sequence set forth in SEQ ID NO: 1, SEQ ID NO 2, or SEQ ID NO: 3, and has immunoglobulin-binding capacity, thereby functioning as an immunoglobulin-binding domain, may be mentioned. Furthermore, the variant has consecutive Asn residue and Lys residue at positions corresponding to the position 3 and position 4 of an amino acid sequence set forth in SEQ ID NO: 1, SEQ ID NO: 2, or SEQ ID NO: 3 in the amino acid sequence of the variant, and has a turn structure composed of these amino acid residues. Examples of the variant of the B domain, Z domain or C domain include a Val1/Ala29 variant of an immunoglobulin-binding domain consisting of an amino acid sequence set forth in SEQ ID NO: 1, SEQ ID NO: 2, or SEQ ID NO: 3.

The variant can be produced by subjecting the B domain, Z domain or C domain of SpA to addition, elimination, substitution, or deletion of amino acid residues, or to modification such as chemical modification of amino acid residues. Examples of the means for addition, elimination, substitution, or deletion of amino acid residues include known means such as site-specific mutation for polynucleotides encoding the above-mentioned domains.

The modified immunoglobulin-binding domain included in the mutated immunoglobulin-binding protein of the present invention is obtained by inserting at least one amino acid residue between an Asn residue at a position corresponding to the position 3 and a Lys residue at a position corresponding to the position 4 of an amino acid sequence of the B domain, Z domain or C domain in the amino acid sequence of the parent domain. For example, the modified immunoglobulin-binding domain is a polypeptide consisting of an amino acid sequence in which at least one amino acid residue is inserted between an Asn residue at the position 3 and a Lys residue at the position 4 of an amino acid sequence of an immunoglobulin-binding domain set forth in SEQ ID NO: 1, SEQ ID NO: 2, or SEQ ID NO: 3. Alternatively, the modified immunoglobulin-binding domain is a polypeptide consisting of an amino acid sequence of an immunoglobulin-binding domain variant having at least 70% identity with an amino acid sequence set forth in SEQ ID NO: 1, SEQ ID NO: 2, or SEQ ID NO: 3 and having consecutive Asn residue and Lys residue at positions corresponding to the position 3 and position 4 of the amino acid sequence set forth in SEQ ID NO: 1, SEQ ID NO: 2, or SEQ ID NO: 3, in which at least one amino acid residue is inserted between the Asn residue and the Lys residue. Such a polypeptide has immunoglobulin-binding capacity and functions as an immunoglobulin-binding domain.

The at least one amino acid residue inserted into the parent domain is not particularly limited; however, for example, the at least one amino acid residue may be at least one, preferably one to four, and more preferably one or two amino acid residues selected from the group consisting of Ala, Arg, Asp, Gln, Glu, His, Met, Thr, Val, Phe, Leu, Ile, Pro, Trp, and Tyr. Among these, Phe, Leu, Ile, and Pro are more preferred; then His, Tyr, and Trp are second preferred; then Arg, Gln, Glu, Asp, Val, and Met are third preferred; and then Thr and Ala are fourth preferred. Therefore, the amino acid residue that is inserted into the parent domain is suitably at least one, preferably one to four, and more preferably one or two selected from the group consisting of Arg, Asp, Gln, Glu, His, Met, Val, Phe, Leu, Ile, Pro, Trp, and Tyr; the amino acid residue is more suitably at least one, preferably one to four, and more preferably one or two selected from the group consisting of His, Phe, Leu, Ile, Pro, Trp, and Tyr; and the amino acid residue is even more suitably at least one, preferably one to four, and more preferably one or two selected from the group consisting of Phe, Leu, Ile, and Pro. The above-mentioned amino acid residues are preferred is speculated to be because the turn structure composed of an Asn residue at the position 3 and a Lys residue at the position 4 is changed, and also, highly alkali-sensitive amino acid sequences represented by Asn-Gly and Asn-Ser can be avoided. When the number of amino acid residues to be inserted is 2 or larger, those amino acid residues may be amino acid residues of all different kinds, or may include multiple amino acid residues of the same kind. More preferably, the amino acid residue to be inserted into the B, Z or C domain, or variants thereof, is any one selected from the group consisting of Phe, Leu, Ile, and Pro.

Regarding the means for inserting an amino acid residue into the parent domain, insertion of a nucleotide sequence encoding the above-mentioned amino acid residue to be inserted, into a nucleotide sequence encoding the parent domain may be mentioned. Specific techniques for inserting a nucleotide sequence include, for example, site-specific mutation, a homologous recombination method, and a SOE (splicing by overlap extension)-PCR method (Gene, 1989, 77:61-68), and detailed procedures of these techniques are well known to those skilled in the art.

It is desirable that the mutated immunoglobulin-binding protein of the present invention include one or more modified immunoglobulin-binding domains each having an amino acid residue inserted between Asn and Lys, and preferably, the mutated immunoglobulin-binding protein includes two or more, more preferably from 2 to 12, and even more preferably from 3 to 8, of the modified immunoglobulin-binding domains. Individual domains are linked to one another. More specifically, the C-terminal of a certain domain is linked to the N-terminal of a neighboring domain, or vice versa. Since the mutated immunoglobulin-binding protein of the present invention has a region in which a plurality of modified immunoglobulin-binding domains is linearly arranged, steric hindrance or immunoglobulin-binding inhibition attributed to the bent arrangement of domains can be prevented. Therefore, the mutated immunoglobulin-binding protein of the present invention has high immunoglobulin-binding capacity.

According to an embodiment, the mutated immunoglobulin-binding protein of the present invention may also include an immunoglobulin-binding domain of SpA other than the B, Z and C domains (for example, A domain, D domain, or E domain) or variants thereof. According to another embodiment, the mutated immunoglobulin-binding protein of the present invention may include B, Z or C domain in which no amino acid residue is inserted between Asn at the position 3 and Lys at the position 4 described above, or variants thereof; however, preferably, the mutated immunoglobulin-binding protein does not include such a domain or a variant. According to a preferred embodiment, all of the immunoglobulin-binding domains that are included in the mutated immunoglobulin-binding protein of the present invention are modified immunoglobulin-binding domains derived from the B, Z or C domain having an amino acid inserted between Asn and Lys, or variants thereof.

According to a preferred embodiment, the mutated immunoglobulin-binding protein of the present invention includes a polypeptide consisting of an amino acid sequence of the B domain set forth in SEQ ID NO: 1, in which one, two, three, or four amino acid residues selected from the group consisting of Ala, Arg, Asp, Gln, Glu, His, Met, Thr, Val, Phe, Leu, Ile, Pro, Trp, and Tyr is inserted between Asn at the position 3 and Lys at the position 4. According to another preferred embodiment, the mutated immunoglobulin-binding protein of the present invention includes a polypeptide consisting of an amino acid sequence of the B domain set forth in SEQ ID NO: 1, in which one to four amino acid residues selected from the group consisting of Phe, Leu, Ile, and Pro is inserted between Asn at the position 3 and Lys at the position 4. According to still another preferred embodiment, the mutated immunoglobulin-binding protein of the present invention includes a polypeptide that functions as an immunoglobulin-binding domain, which includes an amino acid sequence having at least 70% identity with the amino acid sequence of the B domain set forth in SEQ ID NO: 1, in which one, two, three, or four amino acid residues selected from the group consisting of Ala, Arg, Asp, Gln, Glu, His, Met, Thr, Val, Phe, Leu, Ile, Pro, Trp, and Tyr is inserted between Asn-Lys at positions corresponding to the position 3 and the position 4 of SEQ ID NO: 1. According to still another preferred embodiment, the mutated immunoglobulin-binding protein of the present invention is a polypeptide that functions as an immunoglobulin-binding domain, which includes an amino acid sequence having at least 70% identity with the amino acid sequence of the B domain set forth in SEQ ID NO: 1, in which one to four amino acid residues selected from the group consisting of Phe, Leu, Ile, and Pro is inserted between Asn-Lys at positions corresponding to the position 3 and position 4 of SEQ ID NO: 1. According to a still more preferred embodiment, the amino acid sequence having at least 70% identity with the amino acid sequence of the B domain set forth in SEQ ID NO: 1 is an amino acid sequence having a Val1/Ala29 mutation in an amino acid sequence set forth in SEQ ID NO: 1.

According to a preferred embodiment, the mutated immunoglobulin-binding protein of the present invention includes a polypeptide consisting of an amino acid sequence of the Z domain set forth in SEQ ID NO: 2, in which one, two, three, or four amino acid residues selected from the group consisting of Ala, Arg, Asp, Gln, Glu, His, Met, Thr, Val, Phe, Leu, Ile, Pro, Trp, and Tyr is inserted between Asn at the position 3 and Lys at the position 4. According to another preferred embodiment, the mutated immunoglobulin-binding protein of the present invention includes a polypeptide consisting of an amino acid sequence of the Z domain set forth in SEQ ID NO: 2, in which one to four amino acid residues selected from the group consisting of Phe, Leu, Ile, and Pro is inserted between Asn at the position 3 and Lys at the position 4. According to still another preferred embodiment, the mutated immunoglobulin-binding protein of the present invention includes a polypeptide that functions as an immunoglobulin-binding domain, which consists of an amino acid sequence having at least 70% identity with the amino acid sequence of the Z domain set forth in SEQ ID NO: 2, in which one, two, three, or four amino acid residues selected from the group consisting of Ala, Arg, Asp, Gln, Glu, His, Met, Thr, Val, Phe, Leu, Ile, Pro, Trp, and Tyr is inserted between Asn-Lys at positions corresponding to the position 3 and position 4 of SEQ ID NO: 2. According to still another preferred embodiment, the mutated immunoglobulin-binding protein of the present invention includes a polypeptide that functions as an immunoglobulin-binding domain, which consists of an amino acid sequence having at least 70% identity with the amino acid sequence of the Z domain set forth in SEQ ID NO: 2, in which one to four amino acid residues selected from the group consisting of Phe, Leu, Ile, and Pro is inserted between Asn-Lys at positions corresponding to the position 3 and position 4 of SEQ ID NO: 2. According to another preferred embodiment, the amino acid sequence having at least 70% identity the amino acid sequence of the Z domain set forth in SEQ ID NO: 2 is an amino acid sequence having a Val1/Ala29 mutation in the amino acid sequence set forth in SEQ ID NO: 2.

According to a preferred embodiment, the mutated immunoglobulin-binding protein of the present invention includes a polypeptide consisting of an amino acid sequence of the C domain set forth in SEQ ID NO: 3, in which one, two, three, or four amino acid residues selected from the group consisting of Ala, Arg, Asp, Gln, Glu, His, Met, Thr, Val, Phe, Leu, Tle, Pro, Trp, and Tyr is inserted between Asn at the position 3 and Lys at the position 4. According to another preferred embodiment, the mutated immunoglobulin-binding protein of the present invention includes a polypeptide consisting of an amino acid sequence of the C domain set forth in SEQ ID NO: 3, in which one to four amino acid residues selected from the group consisting of Phe, Leu, Ile, and Pro is inserted between Asn at the position 3 and Lys at the position 4. According to still another preferred embodiment, the mutated immunoglobulin-binding protein of the present invention includes a polypeptide that functions as an immunoglobulin-binding domain, which consists of an amino acid sequence having at least 70% identity with the amino acid sequence of the C domain set forth in SEQ ID NO: 3, in which one, two, three, or four amino acid residues selected from the group consisting of Ala, Arg, Asp, Gin, Glu, His, Met, Thr, Val, Phe, Leu, Ile, Pro, Trp, and Tyr is inserted between Asn-Lys at positions corresponding to the position 3 and position 4 of SEQ ID NO: 3. According to still another preferred embodiment, the mutated immunoglobulin-binding protein of the present invention includes a polypeptide that functions as an immunoglobulin-binding domain, which consists of an amino acid sequence having at least 70% identity with the amino acid sequence of the C domain set forth in SEQ ID NO: 3, in which one to four amino acid residues selected from the group consisting of Phe, Leu, Ile, and Pro is inserted between Asn-Lys at positions corresponding to the position 3 and position 4 of SEQ ID NO: 3. According to still another preferred embodiment, the amino acid sequence having at least 70% identity with the amino acid sequence of the C domain set forth in SEQ ID NO: 3 is an amino acid sequence having a Val1/Ala29 mutation in the amino acid sequence set forth in SEQ ID NO: 3.

The polypeptide included in the mutated immunoglobulin-binding protein of the present invention preferably has an amino acid sequence in a state in which Asn-Lys at positions corresponding to the position 3 and position 4 of an amino acid sequence set forth in any one of SEQ ID NO: 1 to SEQ ID NO: 3 are conserved, in which an amino acid is inserted between those residues. More preferably, the mutated immunoglobulin-binding protein of the present invention has an amino acid sequence in a state in which Asp-Asn-Lys or Gln-Asn-Lys at positions corresponding to the position 2 to the position 4 are conserved, in which an amino acid is inserted between the Asn and the Lys. Even more preferably, the mutated immunoglobulin-binding protein of the present invention has an amino acid sequence in a state in which Ala-Asp-Asn-Lys, Gln-Gln-Asn-Lys, or Val-Asp-Asn-Lys at positions corresponding to the position 1 to the position 4 are conserved, in which an amino acid is inserted between the Asn and the Lys. When the Asn at a position corresponding to the position 3 is deleted or mutated, the alkali resistance of the polypeptide may be enhanced; however, the immunoglobulin-binding capacity may be deteriorated.

Preferably, the polypeptide included in the mutated immunoglobulin-binding protein of the present invention has a Val residue at a position corresponding to the position 1 of an amino acid sequence set forth in any one of SEQ ID NO: 1 to SEQ ID NO: 3, and/or has an Ala residue at a position corresponding to the position 29 of an amino acid sequence set forth in any one of SEQ ID NO: 1 to SEQ ID NO: 3.

According to a preferred embodiment, the mutated immunoglobulin-binding protein of the present invention includes from 2 to 12 units, and more preferably from 3 to 8 units, of the polypeptide described above. The respective units of the polypeptide may be identical or different. Preferably, each unit of the polypeptide has its N-terminal linked to the C-terminal of an adjacent polypeptide. The various units of the polypeptide may be directly linked to adjacent polypeptides, or may be linked to adjacent polypeptides via a peptide having 1 to 10 amino acid residues. Examples of this peptide include a peptide represented by EF.

Preferred examples of the mutated immunoglobulin-binding protein of the present invention include polypeptides consisting of amino acid sequences set forth in SEQ ID NO: 4 to SEQ ID NO: 20. Each of the amino acid sequences set forth in SEQ ID NO: 4 to SEQ ID NO: 19 is an amino acid sequence obtained by substituting Ala at the position 1 of an amino acid sequence set forth in SEQ ID NO: 3 with Val and substituting Gly at the position 29 with Ala, in which four variants of the C domain each having one or two amino acid residues selected from the group consisting of Ala, Arg, Asp, Gln, Glu, His, Met, Thr, Val, Phe, Leu, Ile, Pro, Trp, and Tyr inserted between Asn at the position 3 and Lys at the position 4 are linked together. The amino acid sequence set forth in SEQ ID NO: 20 is an amino acid sequence obtained by substituting Ala at the position 1 of an amino acid sequence set forth in SEQ ID NO: 2 with Val and substituting Gly at the position 29 with Ala, in which four variants of the Z domain each having Ile inserted between Asn at the position 3 and Lys at the position 4 are linked together.

Another preferred example of the mutated immunoglobulin-binding protein of the present invention may be a polypeptide having immunoglobulin-binding capacity, the polypeptide consisting of an amino acid sequence having at least 70% identity with an amino acid sequence set forth in any one of SEQ ID NO: 4 to SEQ ID NO: 18, and having Asn-X-Lys (where X represents Ala, Arg, Asp, Gln, Glu, His, Met, Thr, Val, Phe, Leu, Ile, Pro, Trp, or Tyr) disposed respectively at positions corresponding to the position 4 to position 6, the position 63 to position 65, the position 122 to position 124, and the position 181 to position 183 of SEQ ID NO: 4 to 18. Preferably, such a polypeptide has Val at a position corresponding to the position 1 and Ala at a position corresponding to the position 29 of SEQ ID NO: 3.

Another preferred example of the mutated immunoglobulin-binding protein of the present invention may be a polypeptide having immunoglobulin-binding capacity, the polypeptide consisting of an amino acid sequence having at least 70% identity with an amino acid sequence set forth in SEQ ID NO: 19, and having Asn-Ile-Thr-Lys disposed respectively at positions corresponding to the position 4 to position 7, the position 64 to position 67, the position 124 to position 127, and the position 184 to position 187 of SEQ ID NO: 19. Preferably, such a polypeptide has Val at a position corresponding to the position 1 and Ala at a position corresponding to the position 29 of SEQ ID NO: 3.

Another preferred example of the mutated immunoglobulin-binding protein of the present invention may be a polypeptide having immunoglobulin-binding capacity, the polypeptide consisting of an amino acid sequence having at least 70% identity with an amino acid sequence set forth in SEQ ID NO: 20 and having Asn-Ile-Lys disposed respectively at positions corresponding to the position 4 to position 6, the position 63 to position 65, the position 122 to position 124, and the position 181 to position 183 of SEQ ID NO: 20. Preferably, such a polypeptide has Val at a position corresponding to the position 1 and Ala at a position corresponding to the position 29 of SEQ ID NO: 2.

1.2. Polynucleotide and Vector

The present invention also provides a polynucleotide (for example, DNA) encoding the mutated immunoglobulin-binding protein of the present invention described above. A polynucleotide according to an embodiment of the present invention encodes the mutated immunoglobulin-binding protein of the present invention described above, or an isofunctional variant thereof. According to the present specification, the "isofunctional variant" of an immunoglobulin-binding protein means an immunoglobulin-binding protein modified by, for example, partial addition, deletion or substitution of amino acid residues, or chemical modification of amino acid residues, the immunoglobulin-binding protein retaining at least 70% identity with the amino acid sequence of the immunoglobulin-binding protein before modification, maintaining a structure having at least one amino acid residue inserted between Asn-Lys described above, and having immunoglobulin-binding activity that can be considered to be equivalent to that of the immunoglobulin-binding protein before modification.

Furthermore, as described above, the mutated immunoglobulin-binding protein of the present invention includes a protein having one or more, preferably from 2 to 12, and more preferably from 3 to 8, immunoglobulin-binding domains. A polynucleotide encoding such a protein, and an expression plasmid including a vector including that polynucleotide can be produced by known methods.

According to an embodiment, the polynucleotide encoding the mutated immunoglobulin-binding protein of the present invention encodes a polypeptide set forth in any one of SEQ ID NO: 1 to SEQ ID NO: 20. According to another embodiment, the polynucleotide encoding the mutated immunoglobulin-binding protein of the present invention encodes an isofunctional variant of an immunoglobulin-binding protein set forth in any one of SEQ ID NO: 1 to SEQ ID NO: 20. According to another embodiment, the polynucleotide encoding the mutated immunoglobulin-binding protein of the present invention is a polynucleotide consisting of a nucleotide sequence set forth in any one of SEQ ID NO: 23 to SEQ ID NO: 39. According to still another embodiment, the polynucleotide encoding the mutated immunoglobulin-binding protein of the present invention is a polynucleotide encoding an isofunctional variant of an immunoglobulin-binding protein set forth in any one of SEQ ID NO: 4 to SEQ ID NO: 20, the polynucleotide consisting of a nucleotide sequence having at least 70% identity with a nucleotide sequence set forth in any one of SEQ ID NO: 23 to SEQ ID NO: 39.

1.3. Production of Mutated Immunoglobulin-Binding Protein

Regarding standard technologies for producing the mutated immunoglobulin-binding protein of the present invention from the polynucleotide or vector described above, known genetic recombination technologies described in, for example, Current Protocols in Molecular Biology written by Frederick M. Ausbel et al., or Molecular Cloning edited by Sambrook, et al. (Cold Spring Harbor Laboratory Press, 3 edition, 2001) can be utilized. That is, when an expression vector containing a polynucleotide (for example, DNA) encoding the mutated immunoglobulin-binding protein of the present invention is transformed into a host such as *Escherichia coli*, and thus obtained recombinant is cultured in an appropriate liquid medium, an intended modified protein can be obtained economically efficiently in large quantities from the cells after culture. Regarding a preferred expression vector, any of existing vectors capable of duplicating in host cells can be used, and examples include the plasmids described in U.S. Pat. No. 5,151,350 B and the plasmids described in Molecular Cloning edited by Sambrook, et al. (Cold Spring Harbor Laboratory Press, 3rd edition, 2001). Regarding the host for transformation, although there are no particular limitations, known hosts that are used to express recombinant proteins, such as bacteria such as *Escherichia coli*, fungi, insect cells, and mammal cells, can be employed. In order to transform a host by incorporating nucleic acids into the host, any method known in the pertinent technical field may be used according to the various hosts, and for example, the known methods described in, for example, Molecular Cloning edited by Sambrook, et al. (Cold Spring Harbor Laboratory Press, $3^{rd}$ edition, 2001) can be utilized. The methods of culturing a transformed recombinant (for example, a bacterium) and collecting an expressed protein are well known to those skilled in the art, and an example thereof is also described in the Examples of the present invention.

Alternatively, the mutated immunoglobulin-binding protein of the present invention may also be expressed using a cell-free protein synthesis system.

1.4. Carrier

The present invention also provides an affinity carrier having the mutated immunoglobulin-binding protein of the present invention immobilized on a base material (carrier) that is insoluble in water. The shape of the carrier may be a particulate form, and such particles may be porous or non-porous. A particulate carrier can be used as a packed bed, or can also be used in a suspension form. Examples of the suspension form include those known as an expanded bed and a pure suspension, and particles can freely move in the suspension form. In the case of a monolith, a packed bed, and an expanded bed, the procedure for separation generally follows a conventional chromatography method based on concentration gradient. In the case of a pure suspension, a batch method is used. Preferably, this carrier is a packing agent, or the carrier may also be in the form of a chip, a capillary, or a filter. Magnetic particles may also be used as the carrier. The magnetic particles are not particularly limited as long as the particles can be easily magnetized by magnetic induction, and examples include magnetic microparticles formed from triiron tetroxide ($Fe_3O_4$), iron sesquioxide ($\gamma$-$Fe_2O_3$), various ferrites, metals such as iron, manganese, nickel, cobalt, and chromium, and alloys of cobalt, nickel, and manganese; and hydrophobic polymers and hydrophilic polymers containing these magnetic bodies inside the polymers. A suitable example may be the magnetic particles described in JP 2008-32411 A, the magnetic particles having introduced thereinto a polar group containing one or more of at least one kind of atom selected from the group consisting of an oxygen atom, a nitrogen atom, and a sulfur atom, by forming a hydrophobic first polymer layer on the surface of parent particles including superparamagnetic microparticles, forming a second polymer layer having glycidyl groups at least at the surface on the first polymer layer, and chemically modifying the glycidyl group. According to a preferred embodiment, the affinity carrier of the present invention is an affinity chromatography carrier.

The affinity carrier according to an embodiment of the present invention has a particle size of preferably from 10 to 500 μm, and more preferably from 20 to 200 μm. When the carrier is a synthetic polymer, the affinity carrier has a particle size of even more preferably from 20 to 100 μm, and still more preferably from 30 to 80 μm, and when the carrier is a polysaccharide, the affinity carrier has a particle size of even more preferably from 50 to 200 μm, and still more preferably from 60 to 150 μm. When the particle size is less than 10 μm, the column pressure increases at a high flow rate, and the carrier is not durable for practical use. When the particle size is more than 500 μm, there may be occasions in which the amount of immunoglobulins binding to the affinity carrier (binding capacity) is decreased. The "particle size" according to the present specification is the volume average particle size obtainable by a laser diffraction scattering type particle size distribution analyzer.

The affinity carrier according to an embodiment of the present invention is preferably porous, and has a specific surface area of from 50 to 150 $m^2/g$, and more preferably from 80 to 130 $m^2/g$. Here, when the specific surface area is less than 50 $m^2/g$, the binding capacity may be decreased, and when the specific surface area is larger than 150 $m^2/g$, since the strength of the carrier is decreased, the carrier is destroyed at a high flow rate, while the column pressure may increase. The "specific surface area" according to the present specification is a value obtained by dividing the surface area of pores having a pore size of from 10 to 5,000 nm as measured by a mercury porosimeter, by the dry weight of the particles.

The affinity carrier according to an embodiment of the present invention has a volume average pore size of preferably from 100 to 1,400 nm, and when the carrier is a synthetic polymer, the affinity carrier has a volume average pore size of more preferably from 100 to 400 nm, and even more preferably from 200 to 300 nm, while when the carrier is a polysaccharide, the affinity carrier has a volume average pore size of more preferably from 500 to 1,400 nm, and even more preferably from 800 to 1,200 nm. Here, when the volume average pore size is less than 100 nm, a noticeable decrease in the binding capacity at a high flow rate may occur, and when the volume average pore size is more than 1,400 nm, the binding capacity may be lowered irrespective of the flow rate. The "volume average pore size" according to the present specification is the volume average pore size of pores having a pore size of from 10 to 5,000 nm as measured by a mercury porosimeter.

When the carrier satisfies the particle size, the specific surface area, and the pore size distribution in the ranges described above, a balance between the gap between particles serving as flow channels for the solution to be purified as well as the relatively large pore sizes inside the particles, and the binding surface area of the molecules to be purified is optimized, and the binding capacity at a high flow rate is maintained at a high level.

The material for the carrier is, for example, a polymer having a hydrophilic surface, and is a polymer having, for example, a hydroxyl group (—OH), a carboxyl group (—COOH), an aminocarbonyl group (—CONH$_2$ or its N-substituted type), an amino group (—NH$_2$ or its substituted type), or an oligo- or polyethyleneoxy group on the outermost surface (and, if present, also on the innermost surface). According to an embodiment, the polymer may be a synthetic polymer such as polymethacrylate, polyacrylamide, polystyrene, or polyvinyl-alcohol-based polymer, and the polymer is preferably a synthetic polymer such as a crosslinked polymer formed from polyfunctional monomers such as a polyfunctional (meth)acrylate and divinylbenzene. Such synthetic polymers are easily produced by known methods (for example, the method described in J. Mater. Chem., 1991, 1(3), 371-374 may be referred to), or commercially available products such as TOYOPEARL (Tosoh Corp.) are also used. Examples of the polymer according to another embodiment include polysaccharides such as dextran, starch, cellulose, pullulan, and agarose. Such polysaccharides are easily produced by known methods (for example, the method described in JP 4081143 B may be referred to), or commercially available products such as SEPHAROSE (GE Healthcare Biosciences Corp.) are also used. According to another embodiment, the carrier may also be an inorganic carrier such as silica or zirconium oxide.

Regarding the affinity carrier according to an embodiment of the present invention, one specific example of porous particles used as the carrier may be porous organic polymer particles containing, for example, from 10% to 50% by mass of a crosslinkable vinyl monomer and from 3% to 90% by mass of an epoxy group-containing vinyl monomer, and having a particle size of from 20 to 80 μm, a specific surface area of from 50 to 150 m$^2$/g, and a volume average pore size of from 100 to 400 nm.

The intrusion volume (pore volume) of pores having a pore size of from 10 to 5,000 nm when the affinity carrier according to an embodiment of the present invention is measured with a mercury porosimeter is preferably from 1.3 to 7.0 mL/g, and when the carrier is a synthetic polymer, the intrusion volume is more preferably from 1.3 to 2.5 mL/g, while when the carrier is a polysaccharide, the intrusion volume is more preferably from 3.0 to 6.0 mL/g.

1.5. Immobilization of Ligand to Carrier

A method for binding the mutated immunoglobulin-binding protein (ligand) of the present invention to the carrier described above may be carried out using a general method of immobilizing a protein to a carrier. Examples of the means for immobilization include physical adsorption of a ligand to a carrier, and chemical bonding between a carrier and a ligand. Examples of the method for chemical bonding between a carrier and a ligand include a method of using a carrier having a carboxyl group, activating this carboxyl group by means of N-hydroxysuccinimide, and reacting the activated carboxyl group with an amino group of a ligand; a method of using a carrier having an amino group or a carboxyl group, reacting the amino group or carboxyl group with a carboxyl group or an amino group of a ligand in the presence of a dehydration condensation agent such as a water-soluble carbodiimide, and thereby forming an amide bond; a method of using a carrier having a hydroxyl group, activating the hydroxyl group with a cyanogen halide such as cyanogen bromide, and reacting the activated hydroxyl group with an amino group of a ligand; a method of tosylating or tresylating a hydroxyl group of a carrier, and reacting the tosylated or tresylated hydroxyl group with an amino group of a ligand; a method of introducing an epoxy group into a carrier by means of, for example, bisepoxide or epichlorohydrin, and reacting the epoxy group with an amino group, a hydroxyl group, or a thiol group of a ligand; and a method of using a carrier having an epoxy group, and reacting the epoxy group with an amino group, a hydroxyl group, or a thiol group of a ligand. Among the methods described above, from the viewpoint of the stability in an aqueous solution in which the reaction is carried out, a bonding method of introducing a ligand through an epoxy group is desirable.

An alcoholic hydroxyl group, which is a ring-opened epoxy group produced by ring-opening an epoxy group, hydrophilizes the carrier surface and thus accomplishes the roles of preventing non-specific adsorption of, for example, proteins, enhancing the toughness of the carrier in water, and preventing collapse of the carrier at a high flow rate. Therefore, when there are residual epoxy groups that are not bonded to the ligand in the carrier after the immobilization of the ligand, it is preferable to ring-open the residual epoxy groups. Regarding the method for ring-opening an epoxy group in the carrier, for example, a method of stirring the carrier in an aqueous solvent in the presence of acid or alkali under heating or at room temperature may be used. Furthermore, the epoxy group may also be subjected to ring-opening using a blocking agent having a mercapto group, such as mercaptoethanol or thioglycerol, or a blocking agent having an amino group, such as monoethanolamine. The most preferred ring-opened epoxy group is a ring-opened epoxy group obtainable by ring-opening an epoxy group included in a carrier by means of thioglycerol. Thioglycerol is less toxic than mercaptoethanol as a raw material, and a ring-opened epoxy group to which thioglycerol has been added has advantages such as less non-specific adsorption than a group that has been ring-opened by a blocking agent having an amino group, and an increased dynamic binding amount of the carrier.

Furthermore, if necessary, a molecule having an arbitrary length (spacer) may be introduced between a carrier and a ligand. Examples of the spacer include a polymethylene chain, a polyethylene glycol chain, and a sugar. As the spacer, for example, a bifunctional compound that can be chemically bonded to a carrier surface and can also be bonded to a ligand, can be used.

1.6. Operating Effects

The affinity carrier according to an embodiment of the present invention having the mutated immunoglobulin-binding protein of the present invention immobilized thereon has a high initial immunoglobulin dynamic binding capacity (DBC), and does not undergo noticeable deterioration in performance even during cleaning under alkaline conditions (for example, cleaning using an alkaline liquid such as from 0.01 to 0.8 M sodium hydroxide).

2. Method for Isolating Immunoglobulin

A method for isolating an immunoglobulin according to an embodiment of the present invention will be explained. The method for isolating an immunoglobulin according to present embodiment includes a step of bringing a sample containing an immunoglobulin into contact with an affinity carrier having the mutated immunoglobulin-binding protein of the present invention immobilized thereon, and adsorbing the immunoglobulin to the carrier (first step); and a step of eluting the immunoglobulin from the carrier (second step), and preferably, the method further includes a step of cleaning the carrier with an alkaline liquid (third step), after the second step. The affinity carrier of the present invention used in the method for isolating an immunoglobulin of the present invention may be in a suspension form, may be in a state of being packed in a column, or may be in the form of a chip, a capillary, a filter, or magnetic particles.

According to a preferred embodiment, in the first step, a sample containing an immunoglobulin is brought into contact with the affinity carrier of the present invention under the conditions in which the immunoglobulin adsorbs to the ligand. In this first step, most of the substances other than the immunoglobulin in the sample are not adsorbed to the ligand and do not remain on the carrier. Subsequently, if necessary, the carrier may be cleaned with a neutral buffer solution containing a salt such as NaCl, in order to remove some substances weakly held by the ligand.

In the second step, the immunoglobulin adsorbed to the ligand is eluted by causing an appropriate buffer solution at pH 2 to 5 to flow through. By collecting this eluent, the immunoglobulin can be isolated from the sample.

In the method for isolating an immunoglobulin according to the present embodiment, preferably, a third step is carried out subsequently to the second step. In the third step, the carrier is cleaned with an alkaline solution (CIP cleaning). Examples of the alkaline liquid used in the third step include an aqueous solution of sodium hydroxide, an aqueous solution of potassium hydroxide, triethylamine, and tetrabutylammonium hydroxide.

Since the affinity carrier of the present invention stably maintains the immunoglobulin-binding capacity even after the cleaning in the third step due to the enhanced alkali resistance of the protein ligand, the affinity carrier can be repeatedly used in the method for isolating an immunoglobulin of the present invention.

According to an embodiment of the method for isolating an immunoglobulin of the present invention, the immunoglobulin to be isolated may be an antibody or a medicine including an antibody. Therefore, according to an embodiment, the present invention provides a method for producing an antibody medicine using the affinity carrier of the present invention. The procedure of this method is basically the same as the procedure of the method for isolating an immunoglobulin described above, except that a sample containing an intended antibody medicine is used.

EXAMPLES

Hereinafter, the present invention will be more specifically described by way of Examples. Furthermore, the following description is intended to generally disclose the aspects of the present invention, and the present invention is not intended to be limited by such description without any particular reason.

Reference Example 1 Synthesis of Porous Particles 8.2 g of glycidyl methacrylate (manufactured by Mitsubishi Rayon Co., Ltd.), 65.9 g of trimethylolpropane trimethacrylate (manufactured by Sartomer USA, LLC), and 90.6 g of glycerin monomethacrylate (manufactured by NOF Corp.) were dissolved in 245.8 g of 2-octanone (manufactured by Toyo Gosei Co., Ltd.) and 62 g of acetophenone (manufactured by Wako Pure Chemical Industries, Ltd.), and 2 g of 2,2'-azoisobutyronitrile (manufactured by Wako Pure Chemical Industries, Ltd.) was added thereto. Thus, an organic monomer solution was prepared.

Next, 8.5 g of polyvinyl alcohol (PVA-217 manufactured by Kuraray Co., Ltd.), 0.43 g of sodium dodecyl sulfate (EMAL 10G manufactured by Kao Corp.), and 21.3 g of sodium sulfate (manufactured by Wako Pure Chemical Industries, Ltd.) were added to 4240 g of pure water, and the mixture was stirred overnight. Thus, an aqueous solution was prepared.

Next, thus obtained aqueous solution was introduced into a 7-L separable flask, and the flask was equipped with a thermometer, a stirring blade and a cooling tube, and was placed in a hot water bath. Stirring was initiated at 600 rpm. Subsequently, the separable flask was heated by the hot water bath, and when the temperature of the aqueous solution reached 85° C., the organic monomer solution was added to this aqueous solution using a dropping funnel. The resulting mixture was stirred for 5 hours.

Next, the reaction liquid was cooled, and then such reaction liquid was transferred to a 5-L polypropylene jar. The reaction liquid was left to stand until particles floated, and excess water was discarded by suctioning from the lower part. Then, acetone was added to this reaction liquid, and the particles were settled. Next, the reaction liquid was left to stand for 3 minutes, and acetone was removed by decantation. This operation was repeated twice, water was subsequently added thereto, and particles were settled. The reaction liquid was left to stand for another 3 minutes, and decantation was performed. This operation was repeated twice, and particles were cleaned. A dispersion liquid of the particles was purged again with acetone and was dried overnight by blowing air. Subsequently, the particles were dried in a vacuum dryer, and thus 90 g of porous particles (hereinafter, referred to as PB) were obtained. The average particle size of PB was 53 μm, and the specific surface area was 95 m$^2$/g.

Example 1 Production of C Domain Recombinant Type Immunoglobulin-Binding Protein 1 (IgGBPC1)

A plasmid encoding the amino acid sequence set forth in SEQ ID NO: 4 was produced, and *Escherichia coli* competent cells BL21 (DE3) (manufactured by Stratagene Corp.) were transformed using this plasmid. Thus, a recombinant was obtained. Thus obtained recombinant was incubated at 37° C. until the light absorbance (OD600) reached about 10. Subsequently, IPTG (manufactured by Sigma-Aldrich Co.) was added thereto so as to obtain a final concentration of 1 mM, and the mixture was incubated for another 4 hours at 37° C. Thereby, the recombinant type immunoglobulin-binding protein was expressed. After the protein expression, the cells were collected and disrupted in a Tris buffer solution at pH 9.5. The immunoglobulin-binding protein was purified from thus obtained disrupted cell suspension, by anion exchange chromatography (Q-SEPHAROSE FF, manufactured by GE Healthcare Biosciences Corp.) and cation exchange chromatography (SP-SEPHAROSE FF, manufactured by GE Healthcare Biosciences Corp.). The immunoglobulin-binding protein thus purified was dialyzed for 16 hours against a 10 mM citrate buffer solution at pH 6.6. The purity of the immunoglobulin-binding protein checked by SDS-PAGE was 95% or higher. The immunoglobulin-binding protein thus purified was designated as C domain recombinant type immunoglobulin-binding protein 1 (IgGBPC1). This protein contains four variants of the C domain (SEQ ID NO: 3), and has Phe inserted between Asn-Lys at positions corresponding to the position 3 and position 4 of SEQ ID NO: 3 in each variant domain. Furthermore, each of the domains in IgGBPC1 has an alkali resistance-enhancing mutation, A1V/G29A (Protein Science, 2013, 22, 1230-1238).

Examples 2 to 16 Production of C Domain Recombinant Type Immunoglobulin-Binding Proteins 2 to 16 (IgGBPC2 to IgGBPC16)

Plasmids respectively encoding the amino acid sequences set forth in SEQ ID NO: 5 to SEQ ID NO: 19 were produced, and thereafter, recombinant type immunoglobulin-binding proteins 2 to 16 (IgGBPC2 to IgGBPC16) were produced by substantially the same processes as those used in Example 1. Each of these proteins contains four variants of the C domain (SEQ ID NO: 3), and has the amino acid indicated in the following Table 1 inserted between Asn-Lys at positions corresponding to the position 3 and position 4 of SEQ ID NO: 3 in each variant domain. Furthermore, each of the various domains in IgGBPC2 to IgGBPC16 has an alkali resistance-enhancing mutation, A1V/G29A.

Example 17 Production of Z Domain Recombinant Type Immunoglobulin-Binding Protein 1 (IgGBPZ1)

A plasmid encoding the amino acid sequence set forth in SEQ ID NO: 20 was produced, and thereafter, a Z domain recombinant type immunoglobulin-binding protein 1 (IgGBPZ1) was produced by substantially the same processes as those used in Example 1. This protein contains four variants of the Z domain (SEQ ID NO: 2), and has Ile inserted between Asn-Lys at positions corresponding to the position 3 and position 4 of SEQ ID NO: 2 in each variant domain. Furthermore, each of the domains in IgGBPZ1 has an alkali resistance-enhancing mutation, A1V/G29A.

Comparative Example 1 Production of C Domain Recombinant Type Immunoglobulin-Binding Protein 0 (IgGBPC0)

A plasmid encoding the amino acid sequence set forth in SEQ ID NO: 21 was produced, and thereafter, a C domain recombinant type immunoglobulin-binding protein 0 (IgGBPC0) was produced by substantially the same processes as those used in Example 1. This protein contains four variants of the C domain (SEQ ID NO: 3); however, the protein does not have any amino acid residue inserted between Asn-Lys at positions corresponding to the position 3 and position 4 of SEQ ID NO: 3 in each variant domain. Furthermore, IgGBPC0 is a highly alkali-resistant immunoglobulin-binding protein having an alkali resistance-enhancing variant domain, A1V/G29A (Protein Science, 2013, 22, 1230-1238).

Comparative Example 2 Production of Z Domain Recombinant Type Immunoglobulin-Binding Protein 0 (IgGBPZ0)

A plasmid encoding the amino acid sequence set forth in SEQ ID NO: 22 was produced, and thereafter, thereafter, a Z domain recombinant type immunoglobulin-binding protein 0 (IgGSPZ0) was produced by substantially the same processes as those used in Example 1. This protein contains four variants of the Z domain (SEQ ID NO: 2); however, the protein does not have any amino acid residue inserted between Asn-Lys at positions corresponding to the position 3 and position 4 of SEQ ID NO: 2 in each variant domain. Furthermore, IgGBPZ0 is a highly alkali-resistant immunoglobulin-binding protein having an alkali resistance-enhancing variant domain, A1V/G29A (Protein Science, 2013, 22, 1230-1238).

The immunoglobulin-binding proteins of Examples 1 to 17 and Comparative Examples 1 and 2 are presented in Table 1.

TABLE 1

| Example | Name | Base domain | Number of consecutive domains | Mutation introduced between N3 and K4 | Sequence No. |
|---|---|---|---|---|---|
| Comparative Example 1 | IgGBPC0 | C | 4 | None | 21 |
| Comparative Example 2 | IgGBPZ0 | Z | 4 | None | 22 |
| Example 1 | IgGBPC1 | C | 4 | Phe | 4 |
| Example 2 | IgGBPC2 | C | 4 | Leu | 5 |
| Example 3 | IgGBPC3 | C | 4 | Ile | 6 |
| Example 4 | IgGBPC4 | C | 4 | Pro | 7 |
| Example 5 | IgGBPC5 | C | 4 | Gln | 8 |
| Example 6 | IgGBPC6 | C | 4 | His | 9 |
| Example 7 | IgGBPC7 | C | 4 | Arg | 10 |
| Example 8 | IgGBPC8 | C | 4 | Thr | 11 |
| Example 9 | IgGBPC9 | C | 4 | Tyr | 12 |
| Example 10 | IgGBPC10 | C | 4 | Ala | 13 |
| Example 11 | IgGBPC11 | C | 4 | Met | 14 |
| Example 12 | IgGBPC12 | C | 4 | Asp | 15 |
| Example 13 | IgGBPC13 | C | 4 | Trp | 16 |
| Example 14 | IgGBPC14 | C | 4 | Glu | 17 |
| Example 15 | IgGBPC15 | C | 4 | Val | 18 |
| Example 16 | IgGBPC16 | C | 4 | Ile-Thr | 19 |
| Example 17 | IgGBPZ1 | Z | 4 | Ile | 20 |

Test Example 1 Immunoglobulin-Binding Capacity of Affinity Chromatography Carrier 1) Immobilization of Immunoglobulin-Binding Protein on Carrier PB produced in Reference Example 1 was suspended in 150 µL of pure water such that the suspension contained 8 mg of PB, and the suspension was transferred into a filter tube (Millipore Corp.) and centrifuged to eliminate pure water. To this, 450 µL of a 0.1 M carbonate buffer solution pH 9.8 containing 0.85 M sodium sulfate, in which 1 mg of the immunoglobulin-binding protein 1 (IgGBPC1) produced in Example 1 had been dissolved, was added, and the mixture was shaken for 5 hours at 25° C. Thus, the immunoglobulin-binding protein was bound to PB. The particles thus produced were filtered, and then the particles were mixed with 450 µL of 1 M thioglycerol. The particles were caused to react for 16 hours at 25° C., residual epoxy groups were blocked, and the particles were washed with 0.5 M NaOH. Subsequently, the particles were washed with a 0.1 M sodium citrate buffer (pH 3.2) and a 0.1 M sodium phosphate buffer (pH 7.6), and thus 450 µL of bound porous particles (IgGBPC1/PB) were obtained. Porous particles having any one of IgGBPC0, IgGBPC2 to IgGBPC16, and IgGBPZ0 to IgGBPZ1 bound thereto (IgGBPC1/PB to IgGBPC16/PB and IgGBPZ0/PB to IgGBPZ1/PB, respectively) were obtained by the same procedure.

2) Measurement of Amount of Immunoglobulin-Binding Protein Introduced into Carrier For 150 µL of each suspension containing any one of 1 mg of IgGBPC1/PB to IgGBPC16/PB and IgGBPZ0/PB to IgGBPZ1/PB, the amount of incorporation of the immunoglobulin-binding protein bound to the carrier was measured using a BCA Assay kit (Pierce Biotechnology, Inc.)

3) Measurement of IgG Dynamic Binding Capacity

A column having an inner diameter of 0.5 cm was packed with each of IgGBPC0/BP to IgGBPC16/BP and IgGBP0/PB to IgGBPZ1/PB up to a bed height of 20 cm. The column was equilibrated with a 20 mM phosphate buffer (pH 7.5), and then a 20 mM phosphate buffer (pH 7.5) containing human polyclonal IgG (5 mg/mL) was caused to flow through the column at a linear flow rate of 300 cm/hour. The amount of human polyclonal IgG adsorption obtainable when the human polyclonal IgG concentration in the eluate was 10% breakthrough was determined using a light absorbance monitor, and the dynamic binding capacity (DBC) was determined from the carrier volume.

4) Alkali Resistance Test

The carrier-packed column used in section (3) was mounted in AKTA prime plus, and 20 mL of 0.5 M sodium hydroxide was allowed to flow through the column. The column was removed from the apparatus and sealed, and then the column was left to stand for a certain time period (15, 30, or 45 hours) at room temperature. Subsequently, the DBC of human polyclonal IgG was measured at a linear flow rate of 300 cm/hour by the same procedure as in section (3). The binding capacity retention ratio (% DBC) was determined by taking the DBC before treating with 0.5 M sodium hydroxide as 100%.

The amounts of incorporation of the immunoglobulin-binding protein, the DBC, and the results of the alkali resistance test for the various affinity chromatography carriers are presented in Table 2 and Table 3.

TABLE 2

| Carrier name | Ligand | | | | | Amount of ligand binding (mg/mL-particle) | DBC (mg/mL) | DBC after alkali treatment | | | |
|---|---|---|---|---|---|---|---|---|---|---|---|
| | Example | Sequence No. | Base domain | Number of consecutive domains | Mutation introduced between N3 and K4 | | | % DBC Time of immersion in 0.5M NaOH (hr) | | | |
| | | | | | | | | 0 | 15 | 30 | 45 |
| IgGBPC0/PB | Comparative Example 1 | 21 | C | 4 | None | 62 | 46 | 46 100.0 | 38 82.6 | 30 65.2 | 23 50.0 |
| IgGBPZ0/PB | Comparative Example 2 | 22 | Z | 4 | None | 60 | 49 | 49 100.0 | 37 75.5 | 29 59.2 | 23 46.9 |
| IgGBPC1/PB | Example 1 | 4 | C | 4 | Phe | 61 | 51 | 51 100.0 | 42 82.4 | 33 64.7 | 26 51.0 |
| IgGBPC2/PB | Example 2 | 5 | C | 4 | Leu | 61 | 51 | 51 100.0 | 42 82.4 | 34 66.7 | 27 52.9 |
| IgGBPC3/PB | Example 3 | 6 | C | 4 | Ile | 60 | 50 | 50 100.0 | 42 84.0 | 33 66.0 | 27 54.0 |
| IgGBPC4/PB | Example 4 | 7 | C | 4 | Pro | 61 | 50 | 50 100.0 | 42 84.0 | 34 68.0 | 26 52.0 |
| IgGBPC5/PB | Example 5 | 8 | C | 4 | Gln | 60 | 50 | 50 100.0 | 42 84.0 | 33 66.0 | 26 52.0 |
| IgGBPC6/PB | Example 6 | 9 | C | 4 | His | 59 | 50 | 50 100.0 | 42 84.0 | 34 68.0 | 27 54.0 |
| IgGBPC7/PB | Example 7 | 10 | C | 4 | Arg | 61 | 50 | 50 100.0 | 42 84.0 | 32 64.0 | 26 52.0 |
| IgGBPC8/PB | Example 8 | 11 | C | 4 | Thr | 61 | 49 | 49 100.0 | 41 83.7 | 34 69.4 | 27 55.1 |

TABLE 3

| Carrier name | Ligand | | | | | Amount of ligand binding (mg/mL-particle) | DBC (mg/mL) | DBC after alkali treatment | | | |
|---|---|---|---|---|---|---|---|---|---|---|---|
| | Example | Sequence No. | Base domain | Number of consecutive domains | Mutation introduced between N3 and K4 | | | % DBC Time of immersion in 0.5M NaOH (hr) | | | |
| | | | | | | | | 0 | 15 | 30 | 45 |
| IgGBPC9/PB | Example 9 | 12 | C | 4 | Tyr | 60 | 50 | 50 100.0 | 41 82.0 | 33 66.0 | 27 54.0 |
| IgGBPC10/PB | Example 10 | 13 | C | 4 | Ala | 60 | 50 | 50 100.0 | 42 84.0 | 32 64.0 | 27 54.0 |
| IgGBPC11/PB | Example 11 | 14 | C | 4 | Met | 59 | 50 | 50 100.0 | 41 82.0 | 32 64.0 | 26 52.0 |
| IgGBPC12/PB | Example 12 | 15 | C | 4 | Asp | 60 | 49 | 49 100.0 | 40 81.6 | 33 67.3 | 27 55.1 |
| IgGBPC13/PB | Example 13 | 16 | C | 4 | Trp | 61 | 49 | 49 100.0 | 41 83.7 | 32 65.3 | 26 53.1 |
| IgGBPC14/PB | Example 14 | 17 | C | 4 | Glu | 60 | 50 | 50 100.0 | 42 84.0 | 34 68.0 | 26 52.0 |
| IgGBPC15/PB | Example 15 | 18 | C | 4 | Val | 59 | 51 | 51 100.0 | 42 82.4 | 33 64.7 | 26 51.0 |
| IgGBPC16/PB | Example 16 | 19 | C | 4 | Ile-Thr | 60 | 51 | 51 100.0 | 41 80.4 | 33 64.7 | 27 52.9 |
| IgGBPZ1/PB | Example 17 | 20 | Z | 4 | Ile | 62 | 50 | 50 100.0 | 41 82.0 | 33 66.0 | 25 50.0 |

The amounts of binding of the immunoglobulin-binding proteins of Examples 1 to 17 and Comparative Examples 1 to 2 to the carriers were almost equal. Meanwhile, the carriers to which the immunoglobulin-binding proteins of Examples 1 to 17 were immobilized (IgGBPC1/PB to IgGBPC16/PB, and IgGBPZ1/PB) had increased DBC values compared to the carriers to which the protein of Comparative Example 1 or 2 was immobilized (IgGBPC0/PB and IgGBPZ0/PB). Furthermore, even under very harsh alkali conditions involving exposure to 0.5 M sodium hydroxide for up to 45 hours, IgGBPC1/PB to IgGBPC16/PB and IgGBPZ1/PB had high alkali resistance equivalent to that of IgGBPC0/PB or IgGBPZ0/PB, both of which had an alkali resistance-enhancing mutation, and thus relatively high DBC could be retained. Therefore, an affinity chromatography carrier having high DBC and high alkali resistance could be obtained by using an immunoglobulin-binding protein containing a modified domain having an amino acid residue inserted between Asn at the position 3 and Lys at the position 4 of the amino acid sequence of a SpA immunoglobulin-binding domain, as a ligand.

The invention claimed is:

1. An immunoglobulin-binding protein comprising at least one modified immunoglobulin-binding domain,
   wherein the at least one modified immunoglobulin-binding domain is selected from the group consisting of:
   a polypeptide consisting of an amino acid sequence set forth in SEQ ID NO: 1, wherein at least one amino acid residue is inserted in said amino acid sequence between position 3 and position 4 of the amino acid sequence set forth in SEQ ID NO: 1,
   a polypeptide consisting of an amino acid sequence having at least 85% identity with the amino acid sequence set forth in SEQ ID NO: 1, wherein at least one amino acid residue is inserted in said amino acid sequence between positions corresponding to the position 3 and position 4 of the amino acid sequence set forth in SEQ ID NO: 1,
   a polypeptide consisting of an amino acid sequence set forth in SEQ ID NO: 2, wherein at least one amino acid residue is inserted in said amino acid sequence between position 3 and position 4 of the amino acid sequence set forth in SEQ ID NO: 2,
   a polypeptide consisting of an amino acid sequence having at least 85% identity with the amino acid sequence set forth in SEQ ID NO: 2, wherein at least one amino acid residue is inserted in said amino acid sequence between positions corresponding to the position 3 and position 4 of the amino acid sequence set forth in SEQ ID NO: 2,
   a polypeptide consisting of an amino acid sequence set forth in SEQ ID NO: 3, wherein at least one amino acid residue is inserted in said amino acid sequence between position 3 and position 4 of the amino acid sequence set forth in SEQ ID NO: 3, and
   a polypeptide consisting of an amino acid sequence having at least 85% identity with the amino acid sequence set forth in SEQ ID NO: 3, wherein at least one amino acid residue is inserted in said amino acid sequence between positions corresponding to the position 3 and position 4 of the amino acid sequence set forth in SEQ ID NO: 3, and
   wherein the at least one amino acid residue to be inserted is at least one selected from the group consisting of Ala, Arg, Asp, Gln, Glu, His, Met, Thr, Val, Phe, Leu, Ile, Pro, Trp, and Tyr.

2. The immunoglobulin-binding protein according to claim 1, wherein the immunoglobulin-binding domain consisting of an amino acid sequence having at least 85% identity with an amino acid sequence set forth in any one of SEQ ID NO: 1 to SEQ ID NO: 3 is a Val1/Ala29 variant.

3. The immunoglobulin-binding protein according to claim 1, comprising 2 to 12 units of the modified immunoglobulin-binding domain.

4. An affinity carrier comprising the immunoglobulin-binding protein according to claim 1 immobilized on a base material insoluble in water.

5. A method for isolating an immunoglobulin, the method comprising contacting a solution comprising an immunoglobulin with the affinity carrier according to claim 4.

6. A method for producing an antibody medicine, the method comprising contacting a solution comprising an immunoglobulin with the affinity carrier according to claim 4.

7. The immunoglobulin-binding protein according to claim 1, wherein the at least one modified immunoglobulin-binding domain is selected from the group consisting of:
   a polypeptide consisting of an amino acid sequence set forth in SEQ ID NO: 1, wherein at least one amino acid residue is inserted in said amino acid sequence between position 3 and position 4 of the amino acid sequence set forth in SEQ ID NO: 1,
   a polypeptide consisting of an amino acid sequence having at least 90% identity with the amino acid sequence set forth in SEQ ID NO: 1, wherein at least one amino acid residue is inserted in said amino acid sequence between positions corresponding to the position 3 and position 4 of the amino acid sequence set forth in SEQ ID NO: 1,
   a polypeptide consisting of an amino acid sequence set forth in SEQ ID NO: 2, wherein at least one amino acid residue is inserted in said amino acid sequence between position 3 and position 4 of the amino acid sequence set forth in SEQ ID NO: 2,
   a polypeptide consisting of an amino acid sequence having at least 90% identity with the amino acid sequence set forth in SEQ ID NO: 2, wherein at least one amino acid residue is inserted in said amino acid sequence between positions corresponding to the position 3 and position 4 of the amino acid sequence set forth in SEQ ID NO: 2,
   a polypeptide consisting of an amino acid sequence set forth in SEQ ID NO: 3, wherein at least one amino acid residue is inserted in said amino acid sequence between position 3 and position 4 of the amino acid sequence set forth in SEQ ID NO: 3, and
   a polypeptide consisting of an amino acid sequence having at least 90% identity with the amino acid sequence set forth in SEQ ID NO: 3, wherein at least one amino acid residue is inserted in said amino acid sequence between positions corresponding to the position 3 and position 4 of the amino acid sequence set forth in SEQ ID NO: 3, and
   wherein the at least one amino acid residue to be inserted is at least one selected from the group consisting of Ala, Arg, Asp, Gln, Glu, His, Met, Thr, Val, Phe, Leu, Ile, Pro, Trp, and Tyr.

8. A method for producing an immunoglobulin-binding protein, the method comprising:
   inserting, with regard to an amino acid sequence of an immunoglobulin-binding domain at least one amino acid residue between positions corresponding to the position 3 and position 4 of the amino acid sequence of the immunoglobulin-binding domain,
   wherein the immunoglobulin-binding domain is selected from the group consisting of:
   a polypeptide consisting of an amino acid sequence set forth in SEQ ID NO: 1,
   a polypeptide consisting of an amino acid sequence having at least 85% identity with the amino acid sequence set forth in SEQ ID NO: 1,
   a polypeptide consisting of an amino acid sequence set forth in SEQ ID NO: 2,
   a polypeptide consisting of an amino acid sequence having at least 85% identity with the amino acid sequence set forth in SEQ ID NO: 2,
   a polypeptide consisting of an amino acid sequence set forth in SEQ ID NO: 3, and
   a polypeptide consisting of an amino acid sequence having at least 85% identity with the amino acid sequence set forth in SEQ ID NO: 3, and
   wherein the at least one amino acid residue to be inserted is at least one selected from the group consisting of Ala, Arg, Asp, Gln, Glu, His, Met, Thr, Val, Phe, Leu, Ile, Pro, Trp, and Tyr.

9. The method according to claim 8, wherein the immunoglobulin-binding domain consisting of an amino acid sequence having at least 85% identity with the amino acid sequence set forth in any one of SEQ ID NO: 1 to SEQ ID NO: 3 is a Val1/Ala29 variant.

10. The method according to claim 8, further comprising linking 2 to 12 units of the immunoglobulin-binding domain having at least one amino acid residue inserted therein.

11. The method according to claim 8, wherein the immunoglobulin-binding domain is selected from the group consisting of:
   a polypeptide consisting of an amino acid sequence set forth in SEQ ID NO: 1,
   a polypeptide consisting of an amino acid sequence having at least 90% identity with the amino acid sequence set forth in SEQ ID NO: 1,
   a polypeptide consisting of an amino acid sequence set forth in SEQ ID NO: 2,
   a polypeptide consisting of an amino acid sequence having at least 90% identity with the amino acid sequence set forth in SEQ ID NO: 2,
   a polypeptide consisting of an amino acid sequence set forth in SEQ ID NO: 3, and
   a polypeptide consisting of an amino acid sequence having at least 90% identity with the amino acid sequence set forth in SEQ ID NO: 3, and
   wherein the at least one amino acid residue to be inserted is at least one selected from the group consisting of Ala, Arg, Asp, Gln, Glu, His, Met, Thr, Val, Phe, Leu, Ile, Pro, Trp, and Tyr.

12. A method for increasing the immunoglobulin-binding capacity of an immunoglobulin-binding protein, the method comprising:
   inserting, with regard to an amino acid sequence of an immunoglobulin-binding domain at least one amino acid residue between positions corresponding to the position 3 and position 4 of the amino acid sequence of the immunoglobulin-binding domain,
   wherein the immunoglobulin-binding domain is selected from the group consisting of:
   a polypeptide consisting of an amino acid sequence set forth in SEQ ID NO: 1,
   a polypeptide consisting of an amino acid sequence having at least 85% identity with the amino acid sequence set forth in SEQ ID NO: 1, a polypeptide consisting of an amino acid sequence set forth in SEQ ID NO: 2,
a polypeptide consisting of an amino acid sequence having at least 85% identity with the amino acid sequence set forth in SEQ ID NO: 2,
a polypeptide consisting of an amino acid sequence set forth in SEQ ID NO: 3, and
a polypeptide consisting of an amino acid sequence having at least 85% identity with the amino acid sequence set forth in SEQ ID NO: 3, and
wherein the at least one amino acid residue to be inserted is at least one selected from the group consisting of Ala, Arg, Asp, Gln, Glu, His, Met, Thr, Val, Phe, Leu, Ile, Pro, Trp, and Tyr.

13. The method according to claim 12, wherein the immunoglobulin-binding domain is selected from the group consisting of:
a polypeptide consisting of an amino acid sequence set forth in SEQ ID NO: 1,
a polypeptide consisting of an amino acid sequence having at least 90% identity with the amino acid sequence set forth in SEQ ID NO: 1,
a polypeptide consisting of an amino acid sequence set forth in SEQ ID NO: 2,
a polypeptide consisting of an amino acid sequence having at least 90% identity with the amino acid sequence set forth in SEQ ID NO: 2,
a polypeptide consisting of an amino acid sequence set forth in SEQ ID NO: 3, and
a polypeptide consisting of an amino acid sequence having at least 90% identity with the amino acid sequence set forth in SEQ ID NO: 3, and
wherein the at least one amino acid residue to be inserted is at least one selected from the group consisting of Ala, Arg, Asp, Gln, Glu, His, Met, Thr, Val, Phe, Leu, Ile, Pro, Trp, and Tyr.

* * * * *

SEQUENCE LISTING

<160> NUMBER OF SEQ ID NOS: 39

<210> SEQ ID NO 1
<211> LENGTH: 58
<212> TYPE: PRT
<213> ORGANISM: Staphylococcus aureus
<220> FEATURE:
<223> OTHER INFORMATION: Protein A, B domain

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Staphylococcus aureus
<220> FEATURE:
<223> OTHER INFORMATION: Protein A, Z domain

<400> SEQUENCE: 2

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 3
<211> LENGTH: 58
<212> TYPE: PRT
<213> ORGANISM: Staphylococcus aureus
<220> FEATURE:
<223> OTHER INFORMATION: Protein A, C domain

<400> SEQUENCE: 3

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

```
Lys Lys Leu Asn Asp Ala Gln Ala Pro Lys
    50                  55
```

```
<210> SEQ ID NO 4
<211> LENGTH: 237
<212> TYPE: PRT
<213> ORGANISM: Staphylococcus aureus
<220> FEATURE:
<223> OTHER INFORMATION: IgGBPC1

<400> SEQUENCE: 4
```

```
Met Val Asp Asn Phe Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys Val Asp Asn Phe
    50                  55                  60

Lys Phe Asn Lys Glu Gln Gln Asn Ala Phe Tyr Glu Ile Leu His Leu
65                  70                  75                  80

Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Phe Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Phe Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235
```

```
<210> SEQ ID NO 5
<211> LENGTH: 237
<212> TYPE: PRT
<213> ORGANISM: Staphylococcus aureus
<220> FEATURE:
<223> OTHER INFORMATION: IgGBPC2

<400> SEQUENCE: 5
```

```
Met Val Asp Asn Leu Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys Val Asp Asn Leu
    50                  55                  60
```

```
Lys Phe Asn Lys Glu Gln Gln Asn Ala Phe Tyr Glu Ile Leu His Leu
 65                  70                  75                  80

Pro Asn Leu Thr Glu Glu Gln Arg Asn Ala Phe Ile Gln Ser Leu Lys
                 85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Leu Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Leu Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235

<210> SEQ ID NO 6
<211> LENGTH: 237
<212> TYPE: PRT
<213> ORGANISM: Staphylococcus aureus
<220> FEATURE:
<223> OTHER INFORMATION: IgGBPC3

<400> SEQUENCE: 6

Met Val Asp Asn Ile Lys Phe Asn Lys Glu Gln Gln Asn Ala Phe Tyr
 1               5                  10                  15

Glu Ile Leu His Leu Pro Asn Leu Thr Glu Glu Gln Arg Asn Ala Phe
                20                  25                  30

Ile Gln Ser Leu Lys Asp Asp Pro Ser Val Ser Lys Glu Ile Leu Ala
            35                  40                  45

Glu Ala Lys Lys Leu Asn Asp Ala Gln Ala Pro Lys Val Asp Asn Ile
        50                  55                  60

Lys Phe Asn Lys Glu Gln Gln Asn Ala Phe Tyr Glu Ile Leu His Leu
 65                  70                  75                  80

Pro Asn Leu Thr Glu Glu Gln Arg Asn Ala Phe Ile Gln Ser Leu Lys
                 85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Ile Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Ile Lys Phe Asn Lys Glu Gln Gln Asn Ala Phe
            180                 185                 190
```

```
Tyr Glu Ile Leu His Leu Pro Asn Leu Thr Glu Glu Gln Arg Asn Ala
            195                 200                 205

Phe Ile Gln Ser Leu Lys Asp Asp Pro Ser Val Ser Lys Glu Ile Leu
            210                 215                 220

Ala Glu Ala Lys Lys Leu Asn Asp Ala Gln Ala Pro Lys
225                 230                 235

<210> SEQ ID NO 7
<211> LENGTH: 237
<212> TYPE: PRT
<213> ORGANISM: Staphylococcus aureus
<220> FEATURE:
<223> OTHER INFORMATION: IgGBPC4

<400> SEQUENCE: 7

Met Val Asp Asn Pro Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala
            35                  40                  45

Glu Ala Lys Lys Leu Asn Asp Ala Gln Ala Pro Lys Val Asp Asn Pro
        50                  55                  60

Lys Phe Asn Lys Glu Gln Gln Asn Ala Phe Tyr Glu Ile Leu His Leu
65                  70                  75                  80

Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Pro Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Pro Lys Phe Asn Lys Glu Gln Gln Asn Ala Phe
            180                 185                 190

Tyr Glu Ile Leu His Leu Pro Asn Leu Thr Glu Glu Gln Arg Asn Ala
            195                 200                 205

Phe Ile Gln Ser Leu Lys Asp Asp Pro Ser Val Ser Lys Glu Ile Leu
            210                 215                 220

Ala Glu Ala Lys Lys Leu Asn Asp Ala Gln Ala Pro Lys
225                 230                 235

<210> SEQ ID NO 8
<211> LENGTH: 237
<212> TYPE: PRT
<213> ORGANISM: Staphylococcus aureus
<220> FEATURE:
<223> OTHER INFORMATION: IgGBPC5

<400> SEQUENCE: 8

Met Val Asp Asn Gln Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
```

-continued

```
            20                  25                  30
Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys Val Asp Asn Gln
 50                  55                  60

Lys Phe Asn Lys Glu Gln Gln Asn Ala Phe Tyr Glu Ile Leu His Leu
 65                  70                  75                  80

Pro Asn Leu Thr Glu Glu Gln Arg Asn Ala Phe Ile Gln Ser Leu Lys
                 85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Gln Lys Phe Asn Lys Glu
            115                 120                 125

Gln Gln Asn Ala Phe Tyr Glu Ile Leu His Leu Pro Asn Leu Thr Glu
            130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Gln Lys Phe Asn Lys Glu Gln Gln Asn Ala Phe
            180                 185                 190

Tyr Glu Ile Leu His Leu Pro Asn Leu Thr Glu Glu Gln Arg Asn Ala
            195                 200                 205

Phe Ile Gln Ser Leu Lys Asp Asp Pro Ser Val Ser Lys Glu Ile Leu
            210                 215                 220

Ala Glu Ala Lys Lys Leu Asn Asp Ala Gln Ala Pro Lys
225                 230                 235
```

<210> SEQ ID NO 9
<211> LENGTH: 237
<212> TYPE: PRT
<213> ORGANISM: Staphylococcus aureus
<220> FEATURE:
<223> OTHER INFORMATION: IgGBPC6

<400> SEQUENCE: 9

```
Met Val Asp Asn His Lys Phe Asn Lys Glu Gln Gln Asn Ala Phe Tyr
 1               5                  10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys Val Asp Asn His
 50                  55                  60

Lys Phe Asn Lys Glu Gln Gln Asn Ala Phe Tyr Glu Ile Leu His Leu
 65                  70                  75                  80

Pro Asn Leu Thr Glu Glu Gln Arg Asn Ala Phe Ile Gln Ser Leu Lys
                 85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn His Lys Phe Asn Lys Glu
            115                 120                 125

Gln Gln Asn Ala Phe Tyr Glu Ile Leu His Leu Pro Asn Leu Thr Glu
            130                 135                 140

Glu Gln Arg Asn Ala Phe Ile Gln Ser Leu Lys Asp Asp Pro Ser Val
```

145             150             155             160

Ser Lys Glu Ile Leu Ala Glu Ala Lys Lys Leu Asn Asp Ala Gln Ala
                165                 170                 175

Pro Lys Val Asp Asn His Lys Phe Asn Lys Glu Gln Gln Asn Ala Phe
                180                 185                 190

Tyr Glu Ile Leu His Leu Pro Asn Leu Thr Glu Glu Gln Arg Asn Ala
                195                 200                 205

Phe Ile Gln Ser Leu Lys Asp Asp Pro Ser Val Ser Lys Glu Ile Leu
        210                 215                 220

Ala Glu Ala Lys Lys Leu Asn Asp Ala Gln Ala Pro Lys
225                 230                 235

<210> SEQ ID NO 10
<211> LENGTH: 237
<212> TYPE: PRT
<213> ORGANISM: Staphylococcus aureus
<220> FEATURE:
<223> OTHER INFORMATION: IgGBPC7

<400> SEQUENCE: 10

Met Val Asp Asn Arg Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
                20                  25                  30

Ile Gln Ser Leu Lys Asp Asp Pro Ser Val Ser Lys Glu Ile Leu Ala
            35                  40                  45

Glu Ala Lys Lys Leu Asn Asp Ala Gln Ala Pro Lys Val Asp Asn Arg
50                  55                  60

Lys Phe Asn Lys Glu Gln Gln Asn Ala Phe Tyr Glu Ile Leu His Leu
65                  70                  75                  80

Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Arg Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Arg Lys Phe Asn Lys Glu Gln Gln Asn Ala Phe
                180                 185                 190

Tyr Glu Ile Leu His Leu Pro Asn Leu Thr Glu Glu Gln Arg Asn Ala
                195                 200                 205

Phe Ile Gln Ser Leu Lys Asp Asp Pro Ser Val Ser Lys Glu Ile Leu
        210                 215                 220

Ala Glu Ala Lys Lys Leu Asn Asp Ala Gln Ala Pro Lys
225                 230                 235

<210> SEQ ID NO 11
<211> LENGTH: 237
<212> TYPE: PRT
<213> ORGANISM: Staphylococcus aureus
<220> FEATURE:
<223> OTHER INFORMATION: IgGBPC8

<400> SEQUENCE: 11

```
Met Val Asp Asn Thr Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
                20                  25                  30

Ile Gln Ser Leu Lys Asp Asp Pro Ser Val Ser Lys Glu Ile Leu Ala
            35                  40                  45

Glu Ala Lys Lys Leu Asn Asp Ala Gln Ala Pro Lys Val Asp Asn Thr
    50                  55                  60

Lys Phe Asn Lys Glu Gln Gln Asn Ala Phe Tyr Glu Ile Leu His Leu
65                  70                  75                  80

Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Thr Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Thr Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235
```

<210> SEQ ID NO 12
<211> LENGTH: 237
<212> TYPE: PRT
<213> ORGANISM: Staphylococcus aureus
<220> FEATURE:
<223> OTHER INFORMATION: IgGBPC9

<400> SEQUENCE: 12

```
Met Val Asp Asn Tyr Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
                20                  25                  30

Ile Gln Ser Leu Lys Asp Asp Pro Ser Val Ser Lys Glu Ile Leu Ala
            35                  40                  45

Glu Ala Lys Lys Leu Asn Asp Ala Gln Ala Pro Lys Val Asp Asn Tyr
    50                  55                  60

Lys Phe Asn Lys Glu Gln Gln Asn Ala Phe Tyr Glu Ile Leu His Leu
65                  70                  75                  80

Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110
```

Asn Asp Ala Gln Ala Pro Lys Val Asp Asn Tyr Lys Phe Asn Lys Glu
            115                 120                 125

Gln Gln Asn Ala Phe Tyr Glu Ile Leu His Leu Pro Asn Leu Thr Glu
        130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Tyr Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235

<210> SEQ ID NO 13
<211> LENGTH: 237
<212> TYPE: PRT
<213> ORGANISM: Staphylococcus aureus
<220> FEATURE:
<223> OTHER INFORMATION: IgGBPC10

<400> SEQUENCE: 13

Met Val Asp Asn Ala Lys Phe Asn Lys Glu Gln Gln Asn Ala Phe Tyr
1               5                   10                  15

Glu Ile Leu His Leu Pro Asn Leu Thr Glu Gln Arg Asn Ala Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys Val Asp Asn Ala
    50                  55                  60

Lys Phe Asn Lys Glu Gln Gln Asn Ala Phe Tyr Glu Ile Leu His Leu
65                  70                  75                  80

Pro Asn Leu Thr Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Ala Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Ala Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235

<210> SEQ ID NO 14
<211> LENGTH: 237
<212> TYPE: PRT
<213> ORGANISM: Staphylococcus aureus
<220> FEATURE:
<223> OTHER INFORMATION: IgGBPC11

<400> SEQUENCE: 14

Met Val Asp Asn Met Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys Val Asp Asn Met
    50                  55                  60

Lys Phe Asn Lys Glu Gln Gln Asn Ala Phe Tyr Glu Ile Leu His Leu
65                  70                  75                  80

Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Met Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Met Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235

<210> SEQ ID NO 15
<211> LENGTH: 237
<212> TYPE: PRT
<213> ORGANISM: Staphylococcus aureus
<220> FEATURE:
<223> OTHER INFORMATION: IgGBPC12

<400> SEQUENCE: 15

Met Val Asp Asn Asp Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys Val Asp Asn Asp
    50                  55                  60

Lys Phe Asn Lys Glu Gln Gln Asn Ala Phe Tyr Glu Ile Leu His Leu
65                  70                  75                  80

-continued

```
Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Asp Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Asp Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235

<210> SEQ ID NO 16
<211> LENGTH: 237
<212> TYPE: PRT
<213> ORGANISM: Staphylococcus aureus
<220> FEATURE:
<223> OTHER INFORMATION: IgGBPC13

<400> SEQUENCE: 16

Met Val Asp Asn Trp Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
                20                  25                  30

Ile Gln Ser Leu Lys Asp Asp Pro Ser Val Ser Lys Glu Ile Leu Ala
            35                  40                  45

Glu Ala Lys Lys Leu Asn Asp Ala Gln Ala Pro Lys Val Asp Asn Trp
        50                  55                  60

Lys Phe Asn Lys Glu Gln Gln Asn Ala Phe Tyr Glu Ile Leu His Leu
65                  70                  75                  80

Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Trp Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Trp Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205
```

-continued

Phe Ile Gln Ser Leu Lys Asp Asp Pro Ser Val Ser Lys Glu Ile Leu
        210                 215                 220

Ala Glu Ala Lys Lys Leu Asn Asp Ala Gln Ala Pro Lys
225                 230                 235

<210> SEQ ID NO 17
<211> LENGTH: 237
<212> TYPE: PRT
<213> ORGANISM: Staphylococcus aureus
<220> FEATURE:
<223> OTHER INFORMATION: IgGBPC14

<400> SEQUENCE: 17

Met Val Asp Asn Glu Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Pro Lys Val Asp Asn Glu
    50                  55                  60

Lys Phe Asn Lys Glu Gln Gln Asn Ala Phe Tyr Glu Ile Leu His Leu
65                  70                  75                  80

Pro Asn Leu Thr Glu Glu Gln Arg Asn Ala Phe Ile Gln Ser Leu Lys
                85                  90                  95

Asp Asp Pro Ser Val Ser Lys Glu Ile Leu Ala Glu Ala Lys Lys Leu
            100                 105                 110

Asn Asp Ala Gln Ala Pro Lys Val Asp Asn Glu Lys Phe Asn Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Glu Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235

<210> SEQ ID NO 18
<211> LENGTH: 237
<212> TYPE: PRT
<213> ORGANISM: Staphylococcus aureus
<220> FEATURE:
<223> OTHER INFORMATION: IgGBPC15

<400> SEQUENCE: 18

Met Val Asp Asn Val Lys Phe Asn Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Val Ser Lys Glu Ile Leu Ala

```
            35                  40                  45
Glu Ala Lys Lys Leu Asn Asp Ala Gln Ala Pro Lys Val Asp Asn Val
 50                  55                  60

Lys Phe Asn Lys Glu Gln Gln Asn Ala Phe Tyr Glu Ile Leu His Leu
 65                  70                  75                  80

Pro Asn Leu Thr Glu Glu Gln Arg Asn Ala Phe Ile Gln Ser Leu Lys
                 85                  90                  95

Asp Asp Pro Ser Val Ser Lys Glu Ile Leu Ala Glu Ala Lys Lys Leu
             100                 105                 110

Asn Asp Ala Gln Ala Pro Lys Val Asp Asn Val Lys Phe Asn Lys Glu
         115                 120                 125

Gln Gln Asn Ala Phe Tyr Glu Ile Leu His Leu Pro Asn Leu Thr Glu
     130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Asn Val Lys Phe Asn Lys Glu Gln Gln Asn Ala Phe
            180                 185                 190

Tyr Glu Ile Leu His Leu Pro Asn Leu Thr Glu Glu Gln Arg Asn Ala
        195                 200                 205

Phe Ile Gln Ser Leu Lys Asp Asp Pro Ser Val Ser Lys Glu Ile Leu
    210                 215                 220

Ala Glu Ala Lys Lys Leu Asn Asp Ala Gln Ala Pro Lys
225                 230                 235

<210> SEQ ID NO 19
<211> LENGTH: 241
<212> TYPE: PRT
<213> ORGANISM: Staphylococcus aureus
<220> FEATURE:
<223> OTHER INFORMATION: IgGBPC16

<400> SEQUENCE: 19

Met Val Asp Asn Ile Thr Lys Phe Asn Lys Glu Gln Gln Asn Ala Phe
 1               5                  10                  15

Tyr Glu Ile Leu His Leu Pro Asn Leu Thr Glu Glu Gln Arg Asn Ala
                 20                  25                  30

Phe Ile Gln Ser Leu Lys Asp Asp Pro Ser Val Ser Lys Glu Ile Leu
             35                  40                  45

Ala Glu Ala Lys Lys Leu Asn Asp Ala Gln Ala Pro Lys Val Asp Asn
 50                  55                  60

Ile Thr Lys Phe Asn Lys Glu Gln Gln Asn Ala Phe Tyr Glu Ile Leu
 65                  70                  75                  80

His Leu Pro Asn Leu Thr Glu Glu Gln Arg Asn Ala Phe Ile Gln Ser
                 85                  90                  95

Leu Lys Asp Asp Pro Ser Val Ser Lys Glu Ile Leu Ala Glu Ala Lys
             100                 105                 110

Lys Leu Asn Asp Ala Gln Ala Pro Lys Val Asp Asn Ile Thr Lys Phe
         115                 120                 125

Asn Lys Glu Gln Gln Asn Ala Phe Tyr Glu Ile Leu His Leu Pro Asn
     130                 135                 140

Leu Thr Glu Glu Gln Arg Asn Ala Phe Ile Gln Ser Leu Lys Asp Asp
145                 150                 155                 160

Pro Ser Val Ser Lys Glu Ile Leu Ala Glu Ala Lys Lys Leu Asn Asp
```

```
                    165                 170                 175
Ala Gln Ala Pro Lys Val Asp Asn Ile Thr Lys Phe Asn Lys Glu Gln
                180                 185                 190

Gln Asn Ala Phe Tyr Glu Ile Leu His Leu Pro Asn Leu Thr Glu Glu
            195                 200                 205

Gln Arg Asn Ala Phe Ile Gln Ser Leu Lys Asp Asp Pro Ser Val Ser
        210                 215                 220

Lys Glu Ile Leu Ala Glu Ala Lys Lys Leu Asn Asp Ala Gln Ala Pro
225                 230                 235                 240

Lys

<210> SEQ ID NO 20
<211> LENGTH: 237
<212> TYPE: PRT
<213> ORGANISM: Staphylococcus aureus
<220> FEATURE:
<223> OTHER INFORMATION: IgGBPZ1

<400> SEQUENCE: 20

Met Val Asp Asn Ile Lys Phe Asn Lys Glu Gln Gln Asn Ala Phe Tyr
1               5                   10                  15

Glu Ile Leu His Leu Pro Asn Leu Asn Glu Glu Gln Arg Asn Ala Phe
            20                  25                  30

Ile Gln Ser Leu Lys Asp Asp Pro Ser Gln Ser Ala Asn Leu Leu Ala
        35                  40                  45

Glu Ala Lys Lys Leu Asn Asp Ala Gln Ala Pro Lys Val Asp Asn Ile
    50                  55                  60

Lys Phe Asn Lys Glu Gln Gln Asn Ala Phe Tyr Glu Ile Leu His Leu
65                  70                  75                  80

Pro Asn Leu Asn Glu Glu Gln Arg Asn Ala Phe Ile Gln Ser Leu Lys
                85                  90                  95

Asp Asp Pro Ser Gln Ser Ala Asn Leu Leu Ala Glu Ala Lys Lys Leu
            100                 105                 110

Asn Asp Ala Gln Ala Pro Lys Val Asp Asn Ile Lys Phe Asn Lys Glu
        115                 120                 125

Gln Gln Asn Ala Phe Tyr Glu Ile Leu His Leu Pro Asn Leu Asn Glu
    130                 135                 140

Glu Gln Arg Asn Ala Phe Ile Gln Ser Leu Lys Asp Asp Pro Ser Gln
145                 150                 155                 160

Ser Ala Asn Leu Leu Ala Glu Ala Lys Lys Leu Asn Asp Ala Gln Ala
                165                 170                 175

Pro Lys Val Asp Asn Ile Lys Phe Asn Lys Glu Gln Gln Asn Ala Phe
            180                 185                 190

Tyr Glu Ile Leu His Leu Pro Asn Leu Asn Glu Glu Gln Arg Asn Ala
        195                 200                 205

Phe Ile Gln Ser Leu Lys Asp Asp Pro Ser Gln Ser Ala Asn Leu Leu
    210                 215                 220

Ala Glu Ala Lys Lys Leu Asn Asp Ala Gln Ala Pro Lys
225                 230                 235

<210> SEQ ID NO 21
<211> LENGTH: 233
<212> TYPE: PRT
<213> ORGANISM: Staphylococcus aureus
<220> FEATURE:
<223> OTHER INFORMATION: IgGBPC0
```

```
<400> SEQUENCE: 21

Met Val Asp Asn Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys Val Asp Asn Lys Phe
    50                  55                  60

Asn Lys Glu Gln Gln Asn Ala Phe Tyr Glu Ile Leu His Leu Pro Asn
65                  70                  75                  80

Leu Thr Glu Glu Gln Arg Asn Ala Phe Ile Gln Ser Leu Lys Asp Asp
                85                  90                  95

Pro Ser Val Ser Lys Glu Ile Leu Ala Glu Ala Lys Lys Leu Asn Asp
            100                 105                 110

Ala Gln Ala Pro Lys Val Asp Asn Lys Phe Asn Lys Glu Gln Gln Asn
        115                 120                 125

Ala Phe Tyr Glu Ile Leu His Leu Pro Asn Leu Thr Glu Glu Gln Arg
    130                 135                 140

Asn Ala Phe Ile Gln Ser Leu Lys Asp Asp Pro Ser Val Ser Lys Glu
145                 150                 155                 160

Ile Leu Ala Glu Ala Lys Lys Leu Asn Asp Ala Gln Ala Pro Lys Val
                165                 170                 175

Asp Asn Lys Phe Asn Lys Glu Gln Gln Asn Ala Phe Tyr Glu Ile Leu
            180                 185                 190

His Leu Pro Asn Leu Thr Glu Glu Gln Arg Asn Ala Phe Ile Gln Ser
        195                 200                 205

Leu Lys Asp Asp Pro Ser Val Ser Lys Glu Ile Leu Ala Glu Ala Lys
    210                 215                 220

Lys Leu Asn Asp Ala Gln Ala Pro Lys
225                 230

<210> SEQ ID NO 22
<211> LENGTH: 233
<212> TYPE: PRT
<213> ORGANISM: Staphylococcus aureus
<220> FEATURE:
<223> OTHER INFORMATION: IgGBPZ0

<400> SEQUENCE: 22

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys Val Asp Asn Lys Phe
    50                  55                  60

Asn Lys Glu Gln Gln Asn Ala Phe Tyr Glu Ile Leu His Leu Pro Asn
65                  70                  75                  80

Leu Asn Glu Glu Gln Arg Asn Ala Phe Ile Gln Ser Leu Lys Asp Asp
                85                  90                  95

Pro Ser Gln Ser Ala Asn Leu Leu Ala Glu Ala Lys Lys Leu Asn Asp
            100                 105                 110

Ala Gln Ala Pro Lys Val Asp Asn Lys Phe Asn Lys Glu Gln Gln Asn
```

```
              115                 120                 125
Ala Phe Tyr Glu Ile Leu His Leu Pro Asn Leu Asn Glu Glu Gln Arg
        130                 135                 140

Asn Ala Phe Ile Gln Ser Leu Lys Asp Asp Pro Ser Gln Ser Ala Asn
145                 150                 155                 160

Leu Leu Ala Glu Ala Lys Lys Leu Asn Asp Ala Gln Ala Pro Lys Val
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Ala Phe Ile Gln Ser
        195                 200                 205

Leu Lys Asp Asp Pro Ser Gln Ser Ala Asn Leu Leu Ala Glu Ala Lys
        210                 215                 220

Lys Leu Asn Asp Ala Gln Ala Pro Lys
225                 230
```

```
<210> SEQ ID NO 23
<211> LENGTH: 711
<212> TYPE: DNA
<213> ORGANISM: Staphylococcus aureus
<220> FEATURE:
<223> OTHER INFORMATION: IgGBPC1

<400> SEQUENCE: 23
atggtggata actttaaatt taacaaagaa cagcagaacg cgttttatga aattctgcat     60
ctgccgaacc tgaccgaaga acagcgcaac gcgtttattc agagcctgaa agatgatccg    120
agcgtgagca agaaattctg gaagcgaaa aaactgaacg atgcgcaggc gccgaaataa    180
gtggataact ttaaatttaa caagaacag cagaacgcgt ttatgaaat tctgcatctg    240 ccgaacctga ccgaagaaca gcgcaacgcg tttattcaga gcctgaaaga tgatccgagc    300
gtgagcaaag aaattctgga agcgaaaaaa ctgaacgatg cgcaggcgcc gaaataagtg    360
gataacttta aatttaacaa gaacagcag aacgcgtttt atgaaattct gcatctgccg    420
aacctgaccg aagaacagcg caacgcgttt attcagagcc tgaaagatga tccgagcgtg    480
agcaaagaaa ttctggaagc gaaaaaactg aacgatgcgc aggcgccgaa ataagtggat    540
aactttaaat ttaacaaaga acagcagaac gcgtttatg aaattctgca tctgccgaac    600
ctgaccgaag aacagcgcaa cgcgtttatt cagagcctga agatgatcc gagcgtgagc    660 aaagaaattc tggaagcgaa aaaactgaac gatgcgcagg cgccgaaata a             711
```

```
<210> SEQ ID NO 24
<211> LENGTH: 711
<212> TYPE: DNA
<213> ORGANISM: Staphylococcus aureus
<220> FEATURE:
<223> OTHER INFORMATION: IgGBPC2

<400> SEQUENCE: 24
atggtggata acctgaaatt taacaaagaa cagcagaacg cgttttatga aattctgcat     60
ctgccgaacc tgaccgaaga acagcgcaac gcgtttattc agagcctgaa agatgatccg    120
agcgtgagca agaaattctg gaagcgaaa aaactgaacg atgcgcaggc gccgaaataa    180
gtggataacc tgaaatttaa caagaacag cagaacgcgt ttatgaaat tctgcatctg    240 ccgaacctga ccgaagaaca gcgcaacgcg tttattcaga gcctgaaaga tgatccgagc    300
gtgagcaaag aaattctgga agcgaaaaaa ctgaacgatg cgcaggcgcc gaaataagtg    360
```

```
gataacctga aatttaacaa agaacagcag aacgcgtttt atgaaattct gcatctgccg    420
aacctgaccg aagaacagcg caacgcgttt attcagagcc tgaaagatga tccgagcgtg    480
agcaaagaaa ttctggaagc gaaaaaactg aacgatgcgc aggcgccgaa ataagtggat    540
aacctgaaat taacaaaga acagcagaac gcgttttatg aaattctgca tctgccgaac    600
ctgaccgaag aacagcgcaa cgcgtttatt cagagcctga agatgatcc gagcgtgagc    660 aaagaaattc tggaagcgaa aaaactgaac gatgcgcagg cgccgaaata a             711
```

```
<210> SEQ ID NO 25
<211> LENGTH: 711
<212> TYPE: DNA
<213> ORGANISM: Staphylococcus aureus
<220> FEATURE:
<223> OTHER INFORMATION: IgGBPC3

<400> SEQUENCE: 25
atggtggata acattaaatt taacaaagaa cagcagaacg cgttttatga aattctgcat     60
ctgccgaacc tgaccgaaga acagcgcaac gcgtttattc agagcctgaa agatgatccg   120
agcgtgagca agaaattct ggaagcgaaa aaactgaacg atgcgcaggc gccgaaataa    180
gtggataaca ttaaatttaa caagaacag cagaacgcgt tttatgaaat tctgcatctg    240
ccgaacctga ccgaagaaca cgcaacgcg tttattcaga gcctgaaaga tgatccgagc    300
gtgagcaaag aaattctgga agcgaaaaaa ctgaacgatg cgcaggcgcc gaaataagtg    360
gataacatta aatttaacaa agaacagcag aacgcgtttt atgaaattct gcatctgccg    420
aacctgaccg aagaacagcg caacgcgttt attcagagcc tgaaagatga tccgagcgtg    480
agcaaagaaa ttctggaagc gaaaaaactg aacgatgcgc aggcgccgaa ataagtggat    540
aacattaaat taacaaaga acagcagaac gcgttttatg aaattctgca tctgccgaac    600
ctgaccgaag aacagcgcaa cgcgtttatt cagagcctga agatgatcc gagcgtgagc    660 aaagaaattc tggaagcgaa aaaactgaac gatgcgcagg cgccgaaata a            711
```

```
<210> SEQ ID NO 26
<211> LENGTH: 711
<212> TYPE: DNA
<213> ORGANISM: Staphylococcus aureus
<220> FEATURE:
<223> OTHER INFORMATION: IgGBPC4

<400> SEQUENCE: 26
atggtggata acccgaaatt taacaaagaa cagcagaacg cgttttatga aattctgcat     60
ctgccgaacc tgaccgaaga acagcgcaac gcgtttattc agagcctgaa agatgatccg   120
agcgtgagca agaaattct ggaagcgaaa aaactgaacg atgcgcaggc gccgaaataa    180
gtggataacc cgaaatttaa caagaacag cagaacgcgt tttatgaaat tctgcatctg    240
ccgaacctga ccgaagaaca cgcaacgcg tttattcaga gcctgaaaga tgatccgagc    300
gtgagcaaag aaattctgga agcgaaaaaa ctgaacgatg cgcaggcgcc gaaataagtg    360
gataacccga aatttaacaa agaacagcag aacgcgtttt atgaaattct gcatctgccg    420
aacctgaccg aagaacagcg caacgcgttt attcagagcc tgaaagatga tccgagcgtg    480
agcaaagaaa ttctggaagc gaaaaaactg aacgatgcgc aggcgccgaa ataagtggat    540
aacccgaaat taacaaaga acagcagaac gcgttttatg aaattctgca tctgccgaac    600
ctgaccgaag aacagcgcaa cgcgtttatt cagagcctga agatgatcc gagcgtgagc    660 aaagaaattc tggaagcgaa aaaactgaac gatgcgcagg cgccgaaata a            711
```

<210> SEQ ID NO 27
<211> LENGTH: 711
<212> TYPE: DNA
<213> ORGANISM: Staphylococcus aureus
<220> FEATURE:
<223> OTHER INFORMATION: IgGBPC5

<400> SEQUENCE: 27

| | |
|---|---|
| atggtggata accagaaatt taacaaagaa cagcagaacg cgttttatga aattctgcat | 60 |
| ctgccgaacc tgaccgaaga acagcgcaac gcgtttattc agagcctgaa agatgatccg | 120 |
| agcgtgagca aagaaattct ggaagcgaaa aaactgaacg atgcgcaggc gccgaaataa | 180 |
| gtggataacc agaaatttaa caaagaacag cagaacgcgt tttatgaaat tctgcatctg | 240 |
| ccgaacctga ccgaagaaca gcgcaacgcg tttattcaga gcctgaaaga tgatccgagc | 300 |
| gtgagcaaag aaattctgga agcgaaaaaa ctgaacgatg cgcaggcgcc gaaataagtg | 360 |
| gataaccaga aatttaacaa agaacagcag aacgcgtttt atgaaattct gcatctgccg | 420 |
| aacctgaccg aagaacagcg caacgcgttt attcagagcc tgaaagatga tccgagcgtg | 480 |
| agcaaagaaa ttctggaagc gaaaaaactg aacgatgcgc aggcgccgaa ataagtggat | 540 |
| aaccagaaat ttaacaaaga acagcagaac gcgttttatg aaattctgca tctgccgaac | 600 |
| ctgaccgaag aacagcgcaa cgcgtttatt cagagcctga agatgatcc gagcgtgagc | 660 |
| aaagaaattc tggaagcgaa aaaactgaac gatgcgcagg cgccgaaata a | 711 |

<210> SEQ ID NO 28
<211> LENGTH: 711
<212> TYPE: DNA
<213> ORGANISM: Staphylococcus aureus
<220> FEATURE:
<223> OTHER INFORMATION: IgGBPC6

<400> SEQUENCE: 28

| | |
|---|---|
| atggtggata accataaatt taacaaagaa cagcagaacg cgttttatga aattctgcat | 60 |
| ctgccgaacc tgaccgaaga acagcgcaac gcgtttattc agagcctgaa agatgatccg | 120 |
| agcgtgagca aagaaattct ggaagcgaaa aaactgaacg atgcgcaggc gccgaaataa | 180 |
| gtggataacc ataaatttaa caaagaacag cagaacgcgt tttatgaaat tctgcatctg | 240 |
| ccgaacctga ccgaagaaca gcgcaacgcg tttattcaga gcctgaaaga tgatccgagc | 300 |
| gtgagcaaag aaattctgga agcgaaaaaa ctgaacgatg cgcaggcgcc gaaataagtg | 360 |
| gataaccata aatttaacaa agaacagcag aacgcgtttt atgaaattct gcatctgccg | 420 |
| aacctgaccg aagaacagcg caacgcgttt attcagagcc tgaaagatga tccgagcgtg | 480 |
| agcaaagaaa ttctggaagc gaaaaaactg aacgatgcgc aggcgccgaa ataagtggat | 540 |
| aaccataaat ttaacaaaga acagcagaac gcgttttatg aaattctgca tctgccgaac | 600 |
| ctgaccgaag aacagcgcaa cgcgtttatt cagagcctga agatgatcc gagcgtgagc | 660 |
| aaagaaattc tggaagcgaa aaaactgaac gatgcgcagg cgccgaaata a | 711 |

<210> SEQ ID NO 29
<211> LENGTH: 711
<212> TYPE: DNA
<213> ORGANISM: Staphylococcus aureus
<220> FEATURE:
<223> OTHER INFORMATION: IgGBPC7

<400> SEQUENCE: 29

```
atggtggata accgcaaatt taacaaagaa cagcagaacg cgttttatga aattctgcat      60
ctgccgaacc tgaccgaaga acagcgcaac gcgtttattc agagcctgaa agatgatccg     120
agcgtgagca agaaattct ggaagcgaaa aaactgaacg atgcgcaggc gccgaaataa      180
gtggataacc gcaaatttaa caagaacag cagaacgcgt ttatgaaat tctgcatctg      240 ccgaacctga ccgaagaaca gcgcaacgcg tttattcaga gcctgaaaga tgatccgagc     300
gtgagcaaag aaattctgga agcgaaaaaa ctgaacgatg cgcaggcgcc gaaataagtg     360
gataaccgca aatttaacaa agaacagcag aacgcgtttt atgaaattct gcatctgccg     420
aacctgaccg aagaacagcg caacgcgttt attcagagcc tgaaagatga tccgagcgtg     480
agcaaagaaa ttctggaagc gaaaaaactg aacgatgcgc aggcgccgaa ataagtggat     540
aaccgcaaat ttaacaaaga acagcagaac gcgttttatg aaattctgca tctgccgaac     600
ctgaccgaag aacagcgcaa cgcgtttatt cagagcctga agatgatcc gagcgtgagc      660 aaagaaattc tggaagcgaa aaaactgaac gatgcgcagg cgccgaaata a              711

<210> SEQ ID NO 30
<211> LENGTH: 711
<212> TYPE: DNA
<213> ORGANISM: Staphylococcus aureus
<220> FEATURE:
<223> OTHER INFORMATION: IgGBPC8

<400> SEQUENCE: 30
atggtggata caccaaatt taacaaagaa cagcagaacg cgttttatga aattctgcat      60
ctgccgaacc tgaccgaaga acagcgcaac gcgtttattc agagcctgaa agatgatccg     120
agcgtgagca agaaattct ggaagcgaaa aaactgaacg atgcgcaggc gccgaaataa      180
gtggataaca ccaaatttaa caagaacag cagaacgcgt ttatgaaat tctgcatctg      240 ccgaacctga ccgaagaaca gcgcaacgcg tttattcaga gcctgaaaga tgatccgagc     300
gtgagcaaag aaattctgga agcgaaaaaa ctgaacgatg cgcaggcgcc gaaataagtg     360
gataacacca aatttaacaa agaacagcag aacgcgtttt atgaaattct gcatctgccg     420
aacctgaccg aagaacagcg caacgcgttt attcagagcc tgaaagatga tccgagcgtg     480
agcaaagaaa ttctggaagc gaaaaaactg aacgatgcgc aggcgccgaa ataagtggat     540
aacaccaaat ttaacaaaga acagcagaac gcgttttatg aaattctgca tctgccgaac     600
ctgaccgaag aacagcgcaa cgcgtttatt cagagcctga aagatgatcc gagcgtgagc     660
aaagaaattc tggaagcgaa aaaactgaac gatgcgcagg cgccgaaata a              711

<210> SEQ ID NO 31
<211> LENGTH: 711
<212> TYPE: DNA
<213> ORGANISM: Staphylococcus aureus
<220> FEATURE:
<223> OTHER INFORMATION: IgGBPC9

<400> SEQUENCE: 31
atggtggata actataaatt taacaaagaa cagcagaacg cgttttatga aattctgcat      60
ctgccgaacc tgaccgaaga acagcgcaac gcgtttattc agagcctgaa agatgatccg     120
agcgtgagca agaaattct ggaagcgaaa aaactgaacg atgcgcaggc gccgaaataa      180
gtggataact ataaatttaa caagaacag cagaacgcgt ttatgaaat tctgcatctg      240 ccgaacctga ccgaagaaca gcgcaacgcg tttattcaga gcctgaaaga tgatccgagc     300
gtgagcaaag aaattctgga agcgaaaaaa ctgaacgatg cgcaggcgcc gaaataagtg     360
```

```
gataactata aatttaacaa agaacagcag aacgcgtttt atgaaattct gcatctgccg    420
aacctgaccg aagaacagcg caacgcgttt attcagagcc tgaaagatga tccgagcgtg    480
agcaaagaaa ttctggaagc gaaaaaactg aacgatgcgc aggcgccgaa ataagtggat    540
aactataaat taacaaaga acagcagaac gcgttttatg aaattctgca tctgccgaac    600
ctgaccgaag aacagcgcaa cgcgtttatt cagagcctga agatgatccc gagcgtgagc    660
aaagaaattc tggaagcgaa aaaactgaac gatgcgcagg cgccgaaata a             711
```

<210> SEQ ID NO 32
<211> LENGTH: 711
<212> TYPE: DNA
<213> ORGANISM: Staphylococcus aureus
<220> FEATURE:
<223> OTHER INFORMATION: IgGBPC10

<400> SEQUENCE: 32

```
atggtggata acgcgaaatt taacaaagaa cagcagaacg cgttttatga aattctgcat     60
ctgccgaacc tgaccgaaga acagcgcaac gcgtttattc agagcctgaa agatgatccg    120
agcgtgagca aagaaattct ggaagcgaaa aaactgaacg atgcgcaggc gccgaaataa    180
gtggataacg cgaaatttaa caaagaacag cagaacgcgt ttatgaaat tctgcatctg    240 ccgaacctga ccgaagaaca gcgcaacgcg tttattcaga gcctgaaaga tgatccgagc    300
gtgagcaaag aaattctgga agcgaaaaaa ctgaacgatg cgcaggcgcc gaaataagtg    360
gataacgcga aatttaacaa agaacagcag aacgcgtttt atgaaattct gcatctgccg    420
aacctgaccg aagaacagcg caacgcgttt attcagagcc tgaaagatga tccgagcgtg    480
agcaaagaaa ttctggaagc gaaaaaactg aacgatgcgc aggcgccgaa ataagtggat    540
aacgcgaaat ttaacaaaga acagcagaac gcgtttatg aaattctgca tctgccgaac    600
ctgaccgaag aacagcgcaa cgcgtttatt cagagcctga agatgatccc gagcgtgagc    660
aaagaaattc tggaagcgaa aaaactgaac gatgcgcagg cgccgaaata a             711
```

<210> SEQ ID NO 33
<211> LENGTH: 711
<212> TYPE: DNA
<213> ORGANISM: Staphylococcus aureus
<220> FEATURE:
<223> OTHER INFORMATION: IgGBPC11

<400> SEQUENCE: 33

```
atggtggata acatgaaatt taacaaagaa cagcagaacg cgttttatga aattctgcat     60
ctgccgaacc tgaccgaaga acagcgcaac gcgtttattc agagcctgaa agatgatccg    120
agcgtgagca aagaaattct ggaagcgaaa aaactgaacg atgcgcaggc gccgaaataa    180
gtggataaca tgaaatttaa caaagaacag cagaacgcgt ttatgaaat tctgcatctg    240 ccgaacctga ccgaagaaca gcgcaacgcg tttattcaga gcctgaaaga tgatccgagc    300
gtgagcaaag aaattctgga agcgaaaaaa ctgaacgatg cgcaggcgcc gaaataagtg    360
gataacatga aatttaacaa agaacagcag aacgcgtttt atgaaattct gcatctgccg    420
aacctgaccg aagaacagcg caacgcgttt attcagagcc tgaaagatga tccgagcgtg    480
agcaaagaaa ttctggaagc gaaaaaactg aacgatgcgc aggcgccgaa ataagtggat    540
aacatgaaat ttaacaaaga acagcagaac gcgtttatg aaattctgca tctgccgaac    600
ctgaccgaag aacagcgcaa cgcgtttatt cagagcctga agatgatccc gagcgtgagc    660
```
aaagaaattc tggaagcgaa aaaactgaac gatgcgcagg cgccgaaata a        711

<210> SEQ ID NO 34
<211> LENGTH: 711
<212> TYPE: DNA
<213> ORGANISM: Staphylococcus aureus
<220> FEATURE:
<223> OTHER INFORMATION: IgGBPC12

<400> SEQUENCE: 34

```
atggtggata acgataaatt taacaaagaa cagcagaacg cgttttatga aattctgcat        60
ctgccgaacc tgaccgaaga acagcgcaac gcgtttattc agagcctgaa agatgatccg       120
agcgtgagca agaaattct ggaagcgaaa aaactgaacg atgcgcaggc gccgaaataa       180
gtggataacg ataaatttaa caagaacag cagaacgcgt ttatgaaat tctgcatctg        240
ccgaacctga ccgaagaaca gcgcaacgcg tttattcaga gcctgaaaga tgatccgagc       300
gtgagcaaag aaattctgga agcgaaaaaa ctgaacgatg cgcaggcgcc gaaataagtg       360
gataacgata aatttaacaa agaacagcag aacgcgtttt atgaaattct gcatctgccg       420
aacctgaccg aagaacagcg caacgcgttt attcagagcc tgaaagatga tccgagcgtg       480
agcaaagaaa ttctggaagc gaaaaaactg aacgatgcgc aggcgccgaa ataagtggat       540
aacgataaat ttaacaaaga acagcagaac gcgtttatg aaattctgca tctgccgaac       600
ctgaccgaag aacagcgcaa cgcgtttatt cagagcctga agatgatcc gagcgtgagc       660
aaagaaattc tggaagcgaa aaaactgaac gatgcgcagg cgccgaaata a                711
```

<210> SEQ ID NO 35
<211> LENGTH: 711
<212> TYPE: DNA
<213> ORGANISM: Staphylococcus aureus
<220> FEATURE:
<223> OTHER INFORMATION: IgGBPC13

<400> SEQUENCE: 35

```
atggtggata actggaaatt taacaaagaa cagcagaacg cgttttatga aattctgcat        60
ctgccgaacc tgaccgaaga acagcgcaac gcgtttattc agagcctgaa agatgatccg       120
agcgtgagca agaaattct ggaagcgaaa aaactgaacg atgcgcaggc gccgaaataa       180
gtggataact ggaatttaa caagaacag cagaacgcgt ttatgaaat tctgcatctg        240
ccgaacctga ccgaagaaca gcgcaacgcg tttattcaga gcctgaaaga tgatccgagc       300
gtgagcaaag aaattctgga agcgaaaaaa ctgaacgatg cgcaggcgcc gaaataagtg       360
gataactgga aatttaacaa agaacagcag aacgcgtttt atgaaattct gcatctgccg       420
aacctgaccg aagaacagcg caacgcgttt attcagagcc tgaaagatga tccgagcgtg       480
agcaaagaaa ttctggaagc gaaaaaactg aacgatgcgc aggcgccgaa ataagtggat       540
aactggaaat ttaacaaaga acagcagaac gcgtttatg aaattctgca tctgccgaac       600
ctgaccgaag aacagcgcaa cgcgtttatt cagagcctga agatgatcc gagcgtgagc       660
aaagaaattc tggaagcgaa aaaactgaac gatgcgcagg cgccgaaata a                711
```

<210> SEQ ID NO 36
<211> LENGTH: 711
<212> TYPE: DNA
<213> ORGANISM: Staphylococcus aureus
<220> FEATURE:
<223> OTHER INFORMATION: IgGBPC14

<400> SEQUENCE: 36

| | |
|---|---|
| atggtggata acgaaaaatt taacaaagaa cagcagaacg cgttttatga aattctgcat | 60 |
| ctgccgaacc tgaccgaaga acagcgcaac gcgtttattc agagcctgaa agatgatccg | 120 |
| agcgtgagca agaaaattct ggaagcgaaa aaactgaacg atgcgcaggc gccgaaataa | 180 |
| gtggataacg aaaaatttaa caaagaacag cagaacgcgt tttatgaaat tctgcatctg | 240 |
| ccgaacctga ccgaagaaca gcgcaacgcg tttattcaga gcctgaaaga tgatccgagc | 300 |
| gtgagcaaag aaattctgga agcgaaaaaa ctgaacgatg cgcaggcgcc gaaataagtg | 360 |
| gataacgaaa aatttaacaa agaacagcag aacgcgtttt atgaaattct gcatctgccg | 420 |
| aacctgaccg aagaacagcg caacgcgttt attcagagcc tgaaagatga tccgagcgtg | 480 |
| agcaaagaaa ttctggaagc gaaaaaactg aacgatgcgc aggcgccgaa ataagtggat | 540 |
| aacgaaaaat taacaaaga acagcagaac gcgttttatg aaattctgca tctgccgaac | 600 |
| ctgaccgaag aacagcgcaa cgcgtttatt cagagcctga agatgatccc gagcgtgagc | 660 |
| aaagaaattc tggaagcgaa aaaactgaac gatgcgcagg cgccgaaata a | 711 |

<210> SEQ ID NO 37
<211> LENGTH: 711
<212> TYPE: DNA
<213> ORGANISM: Staphylococcus aureus
<220> FEATURE:
<223> OTHER INFORMATION: IgGBPC15

<400> SEQUENCE: 37

| | |
|---|---|
| atggtggata acgtgaaatt taacaaagaa cagcagaacg cgttttatga aattctgcat | 60 |
| ctgccgaacc tgaccgaaga acagcgcaac gcgtttattc agagcctgaa agatgatccg | 120 |
| agcgtgagca agaaaattct ggaagcgaaa aaactgaacg atgcgcaggc gccgaaataa | 180 |
| gtggataacg tgaaatttaa caaagaacag cagaacgcgt tttatgaaat tctgcatctg | 240 |
| ccgaacctga ccgaagaaca gcgcaacgcg tttattcaga gcctgaaaga tgatccgagc | 300 |
| gtgagcaaag aaattctgga agcgaaaaaa ctgaacgatg cgcaggcgcc gaaataagtg | 360 |
| gataacgtga aatttaacaa agaacagcag aacgcgtttt atgaaattct gcatctgccg | 420 |
| aacctgaccg aagaacagcg caacgcgttt attcagagcc tgaaagatga tccgagcgtg | 480 |
| agcaaagaaa ttctggaagc gaaaaaactg aacgatgcgc aggcgccgaa ataagtggat | 540 |
| aacgtgaaat ttaacaaaga acagcagaac gcgttttatg aaattctgca tctgccgaac | 600 |
| ctgaccgaag aacagcgcaa cgcgtttatt cagagcctga agatgatccc gagcgtgagc | 660 |
| aaagaaattc tggaagcgaa aaaactgaac gatgcgcagg cgccgaaata a | 711 |

<210> SEQ ID NO 38
<211> LENGTH: 723
<212> TYPE: DNA
<213> ORGANISM: Staphylococcus aureus
<220> FEATURE:
<223> OTHER INFORMATION: IgGBPC16

<400> SEQUENCE: 38

| | |
|---|---|
| atggtggata acattaccaa atttaacaaa gaacagcaga acgcgtttta tgaaattctg | 60 |
| catctgccga acctgaccga agaacagcgc aacgcgttta ttcagagcct gaaagatgat | 120 |
| ccgagcgtga gcaaagaaat tgcggaagcg aaaaaactga acgatgcgca ggcgccgaaa | 180 |
| taagtggata acattaccaa atttaacaaa gaacagcaga acgcgtttta tgaaattctg | 240 |
| catctgccga acctgaccga agaacagcgc aacgcgttta ttcagagcct gaaagatgat | 300 |

-continued

```
ccgagcgtga gcaaagaaat tgcggaagcg aaaaaactga acgatgcgca ggcgccgaaa      360
taagtggata acattaccaa atttaacaaa gaacagcaga acgcgtttta tgaaattctg      420
catctgccga acctgaccga agaacagcgc aacgcgttta ttcagagcct gaaagatgat      480
ccgagcgtga gcaaagaaat tgcggaagcg aaaaaactga acgatgcgca ggcgccgaaa      540
taagtggata acattaccaa atttaacaaa gaacagcaga acgcgtttta tgaaattctg      600
catctgccga acctgaccga agaacagcgc aacgcgttta ttcagagcct gaaagatgat      660
ccgagcgtga gcaaagaaat tgcggaagcg aaaaaactga acgatgcgca ggcgccgaaa      720
taa                                                                     723

<210> SEQ ID NO 39
<211> LENGTH: 711
<212> TYPE: DNA
<213> ORGANISM: Staphylococcus aureus
<220> FEATURE:
<223> OTHER INFORMATION: IgGBPZ1

<400> SEQUENCE: 39
atggtggata acattaaatt taacaaagaa cagcagaacg cgttttatga aattctgcat      60
ctgccgaacc tgaacgaaga acagcgcaac gcgtttattc agagcctgaa agatgatccg     120
agccagagcg cgaacctgct ggaagcgaaa aaactgaacg atgcgcaggc gccgaaataa     180
gtggataaca ttaaatttaa caagaacag cagaacgcgt tttatgaaat tctgcatctg     240
ccgaacctga cgaagaaca gcgcaacgcg tttattcaga gcctgaaaga tgatccgagc     300
cagagcgcga acctgctgga agcgaaaaaa ctgaacgatg cgcaggcgcc gaaataagtg     360
gataacatta aatttaacaa gaacagcag aacgcgtttt atgaaattct gcatctgccg     420
aacctgaacg aagaacagcg caacgcgttt attcagagcc tgaaagatga tccgagccag     480
agcgcgaacc tgctggaagc gaaaaaactg aacgatgcgc aggcgccgaa ataagtggat     540
aacattaaat ttaacaaaga acagcagaac gcgttttatg aaattctgca tctgccgaac     600
ctgaacgaag aacagcgcaa cgcgtttatt cagagcctga agatgatcc gagccagagc     660 gcgaacctgc tggaagcgaa aaaactgaac gatgcgcagg cgccgaaata a              711
```